(12) United States Patent
Bar

(10) Patent No.: US 12,029,511 B2
(45) Date of Patent: Jul. 9, 2024

(54) BILATERAL SURGICAL ROBOTIC SYSTEM

(71) Applicant: LEM Surgical AG, Bern (CH)

(72) Inventor: Yossi Bar, Muri bei Bern (CH)

(73) Assignee: LEM Surgical AG, Bern (CH)

( * ) Notice: Subject to any disclaimer, the term of this patent is extended or adjusted under 35 U.S.C. 154(b) by 0 days.

(21) Appl. No.: 18/217,595

(22) Filed: Jul. 2, 2023

(65) Prior Publication Data

US 2023/0380916 A1    Nov. 30, 2023

Related U.S. Application Data

(63) Continuation of application No. PCT/IB2022/052297, filed on Mar. 14, 2022.
(Continued)

(51) Int. Cl.
*A61B 34/32* (2016.01)
*A61B 34/00* (2016.01)
(Continued)

(52) U.S. Cl.
CPC .............. *A61B 34/32* (2016.02); *A61B 34/25* (2016.02); *A61B 50/13* (2016.02); *A61B 90/50* (2016.02);
(Continued)

(58) Field of Classification Search
CPC ......... A61B 34/32; A61B 34/25; A61B 50/13; A61B 90/50; A61B 2034/2055; A61B 2090/3966; B25J 9/1682
(Continued)

(56) References Cited

U.S. PATENT DOCUMENTS 10,512,509 B2 * 12/2019 Bowling ................ A61B 17/02
11,638,618 B2 * 5/2023 Schuh .................... A61B 34/71
606/1
(Continued)

FOREIGN PATENT DOCUMENTS

CN    109 549 706    4/2019
CN    111 700 684    9/2020
(Continued)

OTHER PUBLICATIONS

Co-pending U.S. Appl. No. 18/282,787, inventor Bar; Yossi, filed Sep. 18, 2023.
(Continued)

*Primary Examiner* — Aaron F Roane
(74) *Attorney, Agent, or Firm* — Wilson Sonsini Goodrich & Rosati

(57) ABSTRACT

A mobile bilateral robotic surgery system is provided. The system may be optimized for robotic spinal surgery. The system comprises a mobile cart configured to be deployable under a surgical table, and particular a spinal surgery table. The mobile cart does not need to be affixed to the floor or the surgical table. The cart comprises multiple robotic arms that can be folded beside or into the cart so as to allow for deployment under the surgical table. The robotic arms may be relatively short and light compared to known systems and are deployed to either side of the patient. This allows for the highly accurate performance of a wide range of surgical procedures. The mobile cart further comprises a central control unit that facilitates the system knowing the position of the robotic arms. The system further optionally comprises a robotic navigation capability that augments the abilities of the system in locating features of a patient's anatomy and tools being used in a surgical procedure.

16 Claims, 27 Drawing Sheets

Related U.S. Application Data

(60) Provisional application No. 63/253,533, filed on Oct. 7, 2021, provisional application No. 63/161,716, filed on Mar. 16, 2021.

(51) Int. Cl.
*A61B 50/13* (2016.01)
*A61B 90/50* (2016.01)
*B25J 9/16* (2006.01)
*A61B 34/20* (2016.01)
*A61B 90/00* (2016.01)

(52) U.S. Cl.
CPC ..... *B25J 9/1682* (2013.01); *A61B 2034/2055* (2016.02); *A61B 2090/3966* (2016.02)

(58) Field of Classification Search
USPC .............................................. 606/1
See application file for complete search history.

(56) References Cited

U.S. PATENT DOCUMENTS

| | | |
|---|---|---|
| 2010/0286712 A1 | 11/2010 | Won et al. |
| 2018/0193101 A1 | 7/2018 | Hashimoto |
| 2018/0362060 A1 | 12/2018 | Schaller |
| 2019/0008598 A1 | 1/2019 | Frimer |

FOREIGN PATENT DOCUMENTS

| | | |
|---|---|---|
| WO | WO2018/222470 | 12/2018 |
| WO | WO2018/236594 | 12/2018 |
| WO | WO2020/079596 | 4/2020 |
| WO | WO-2022195460 A1 | 9/2022 |

OTHER PUBLICATIONS

PCT/IB2022/052297 International Search Report and Written Opinion dated Jun. 14, 2022.

\* cited by examiner

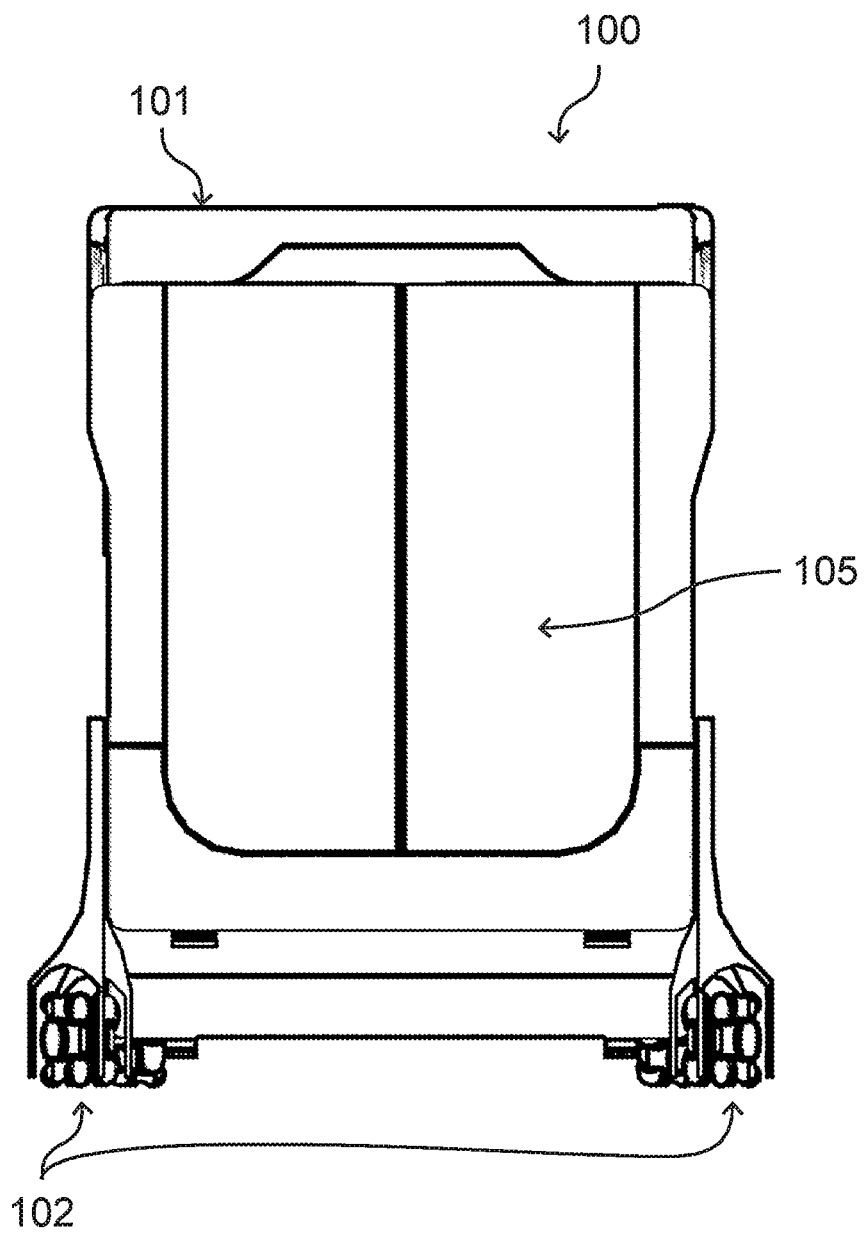

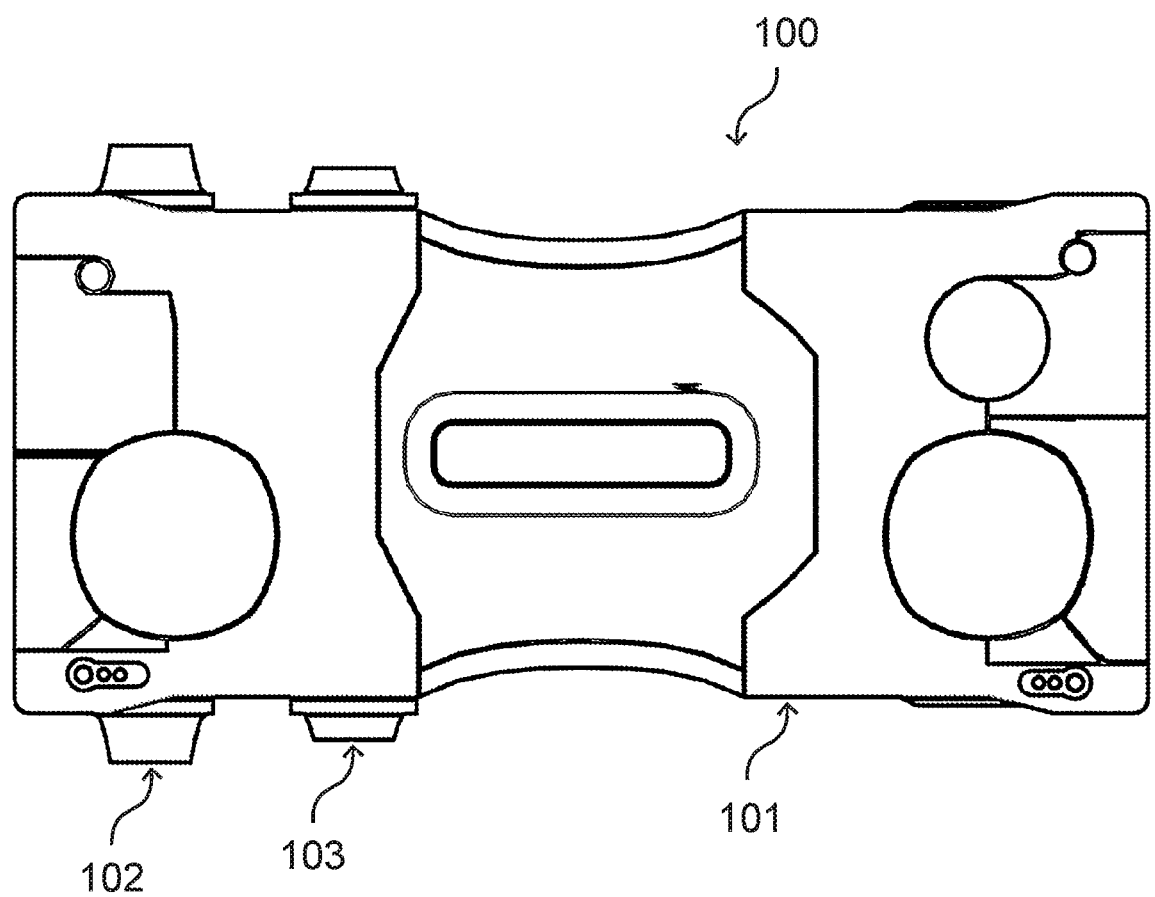

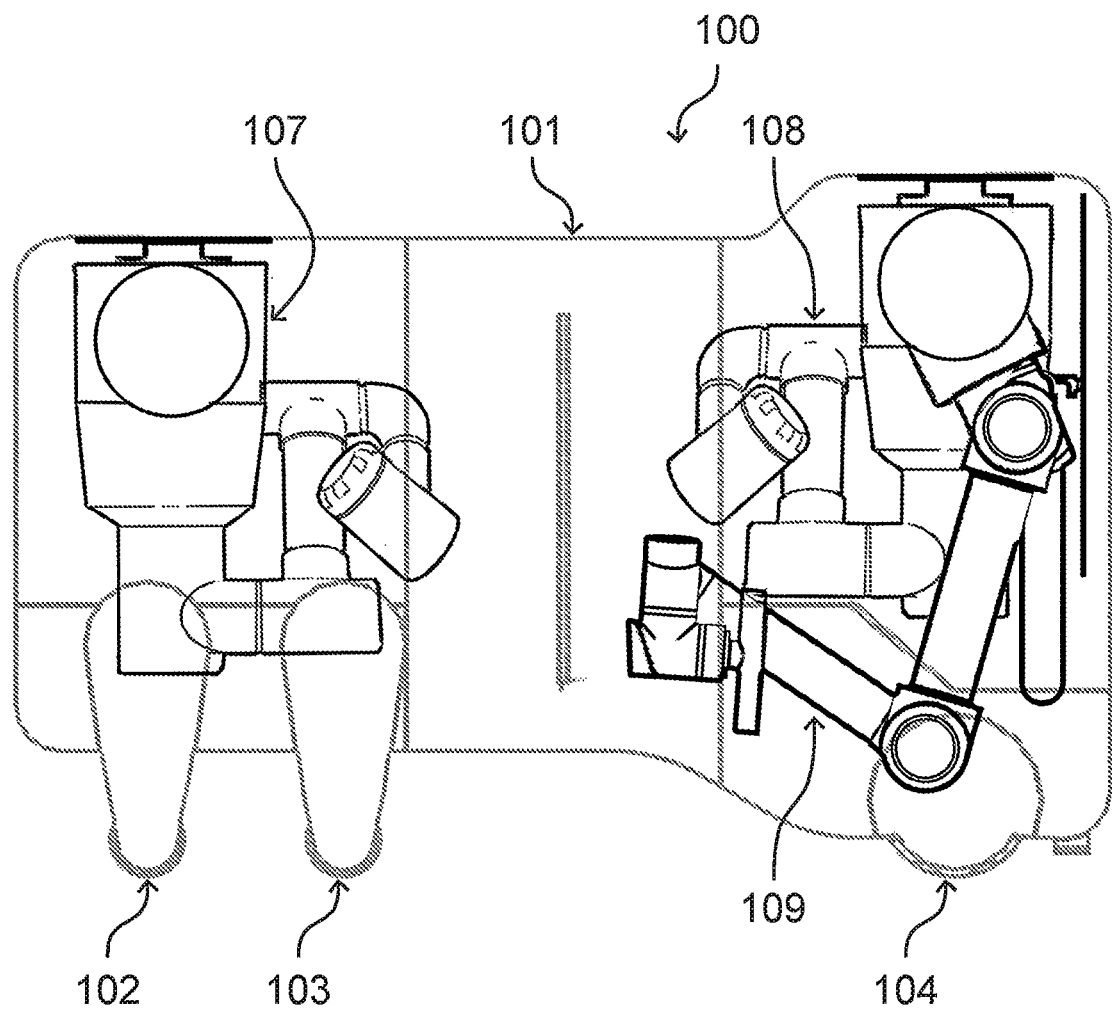

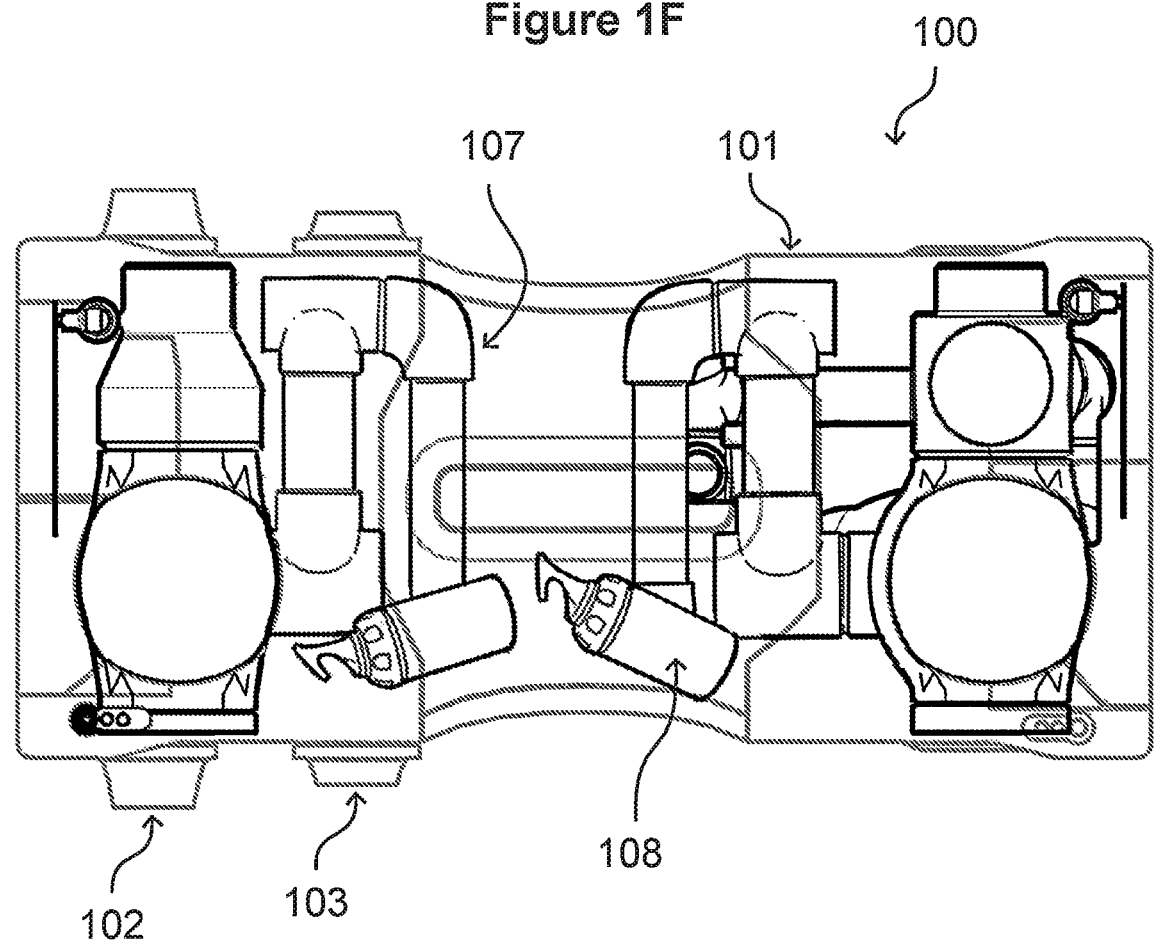

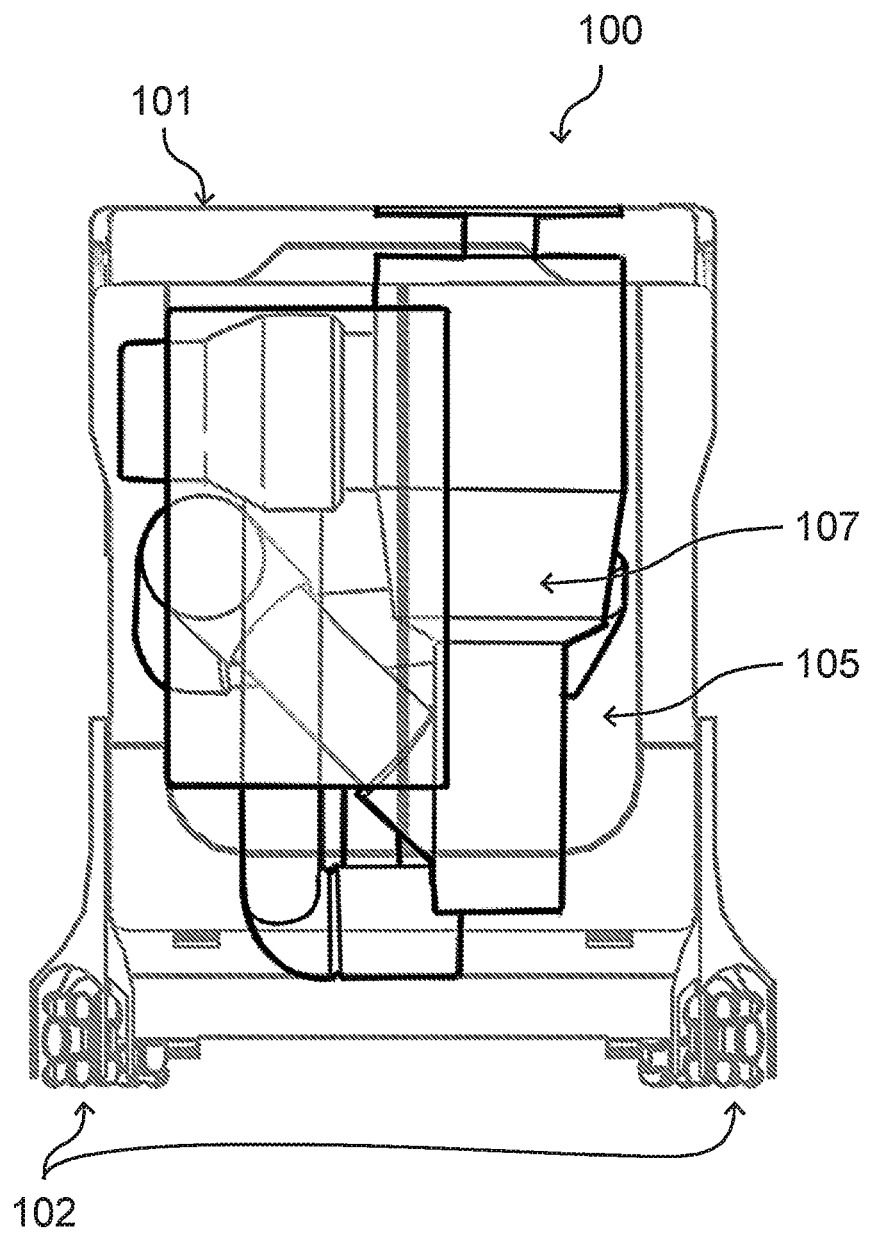

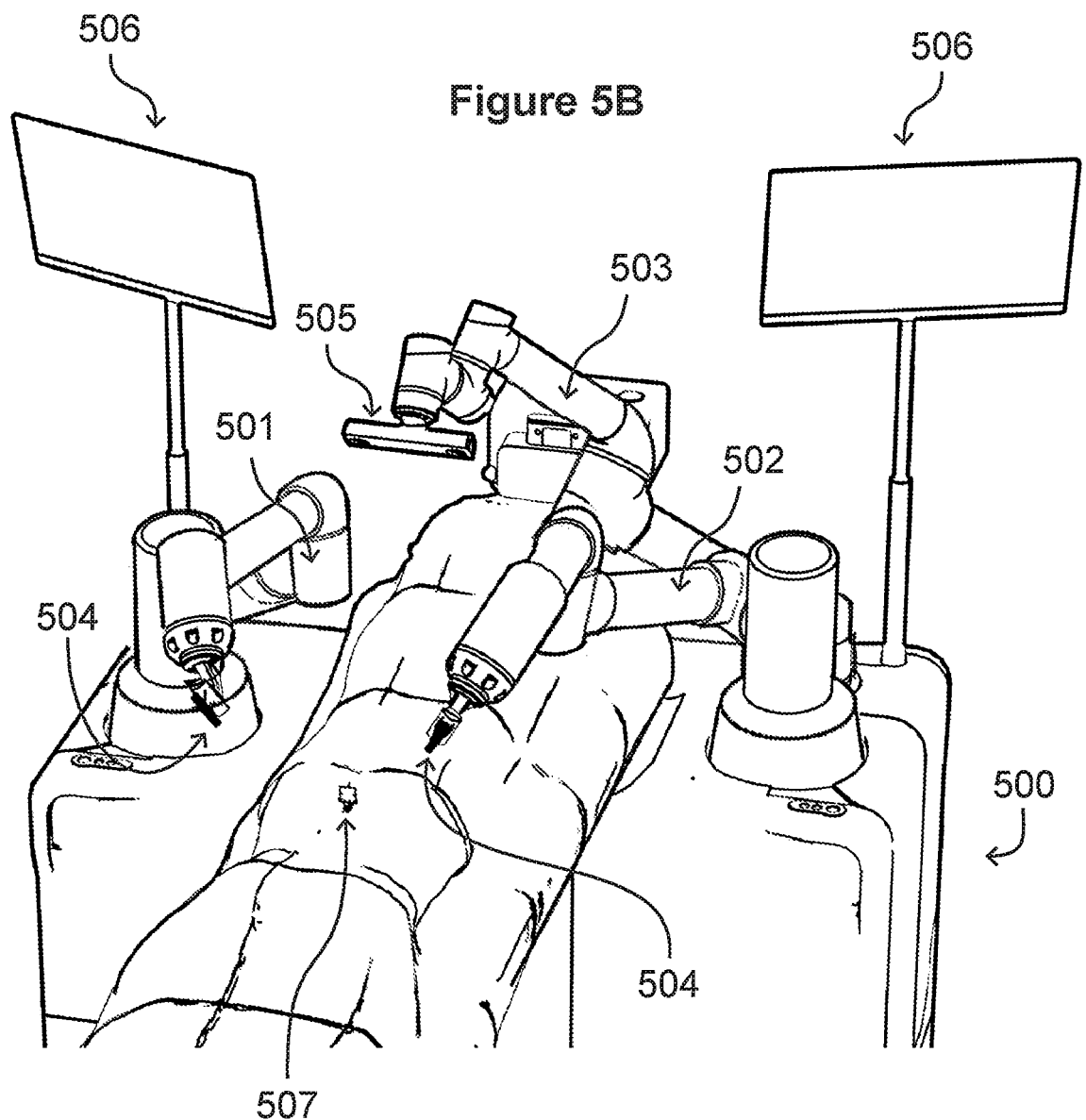

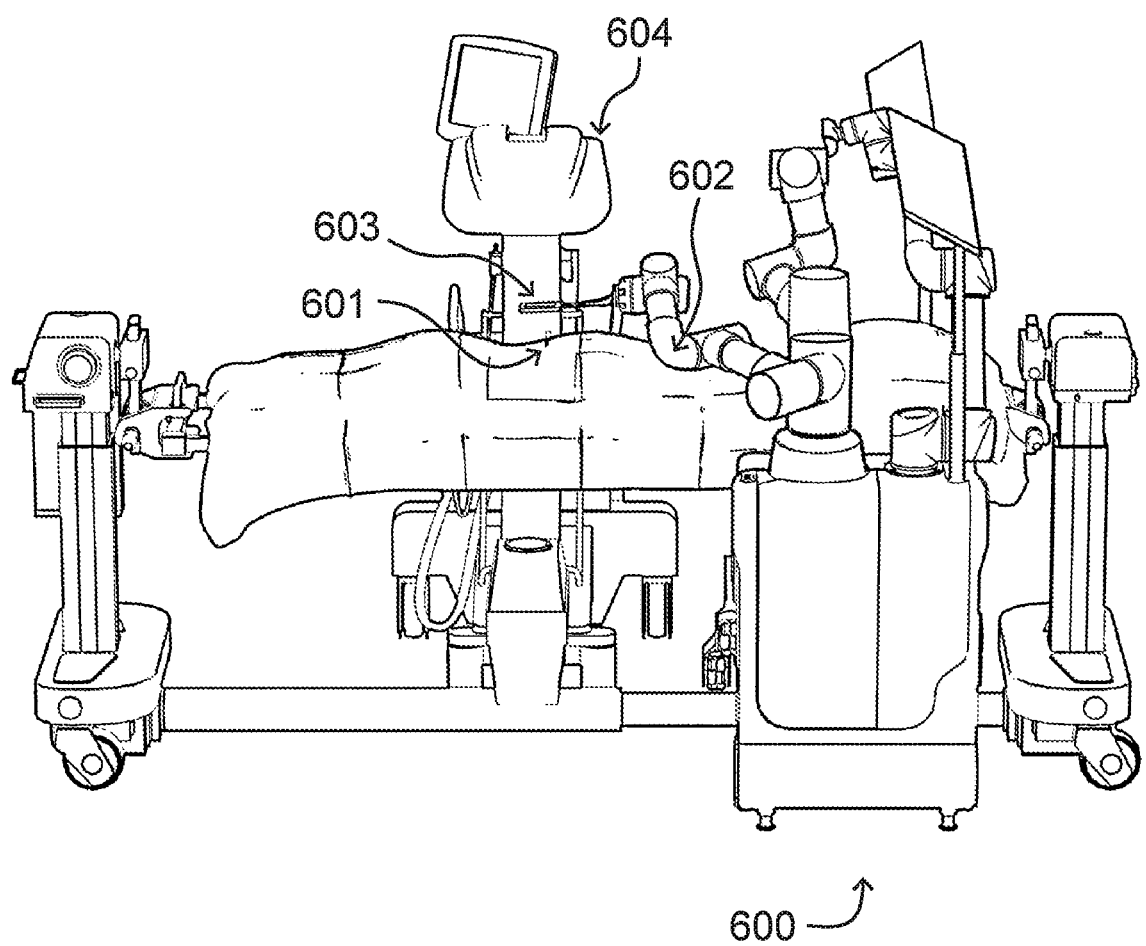

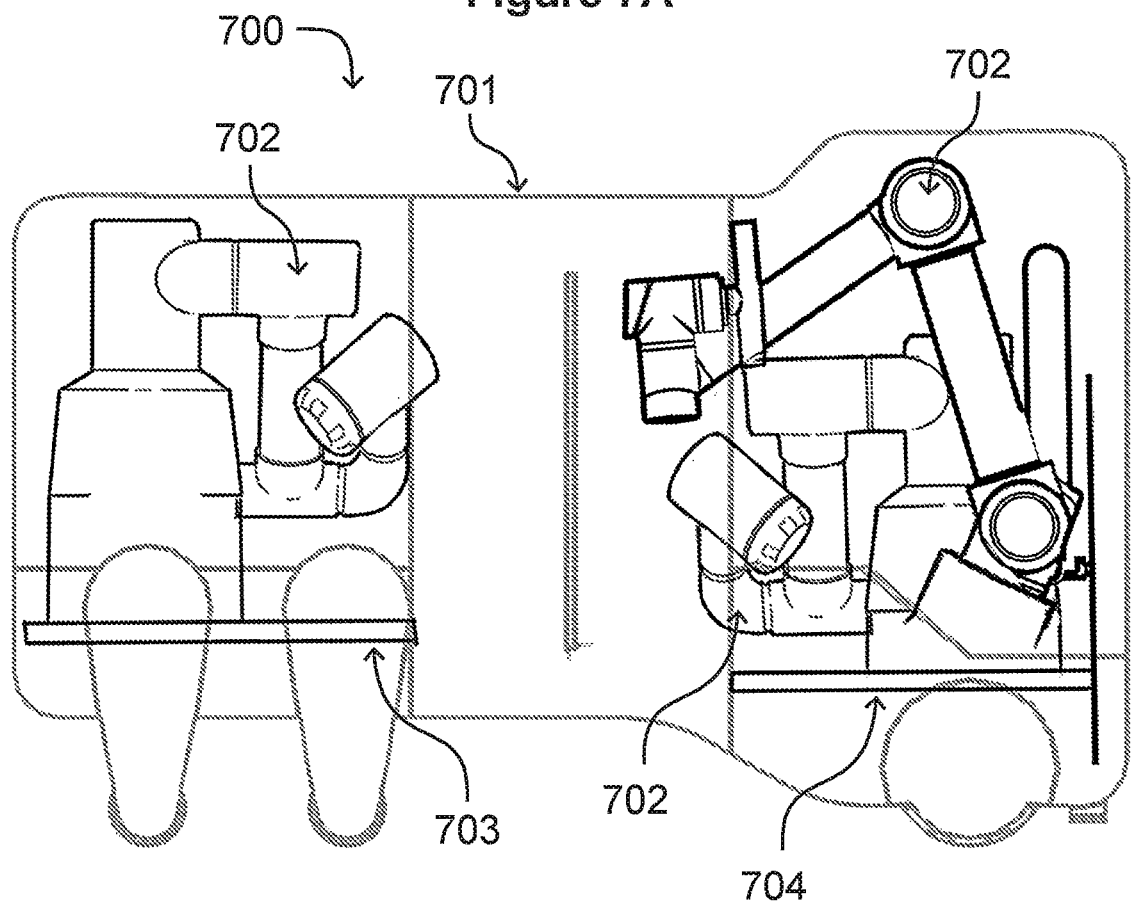

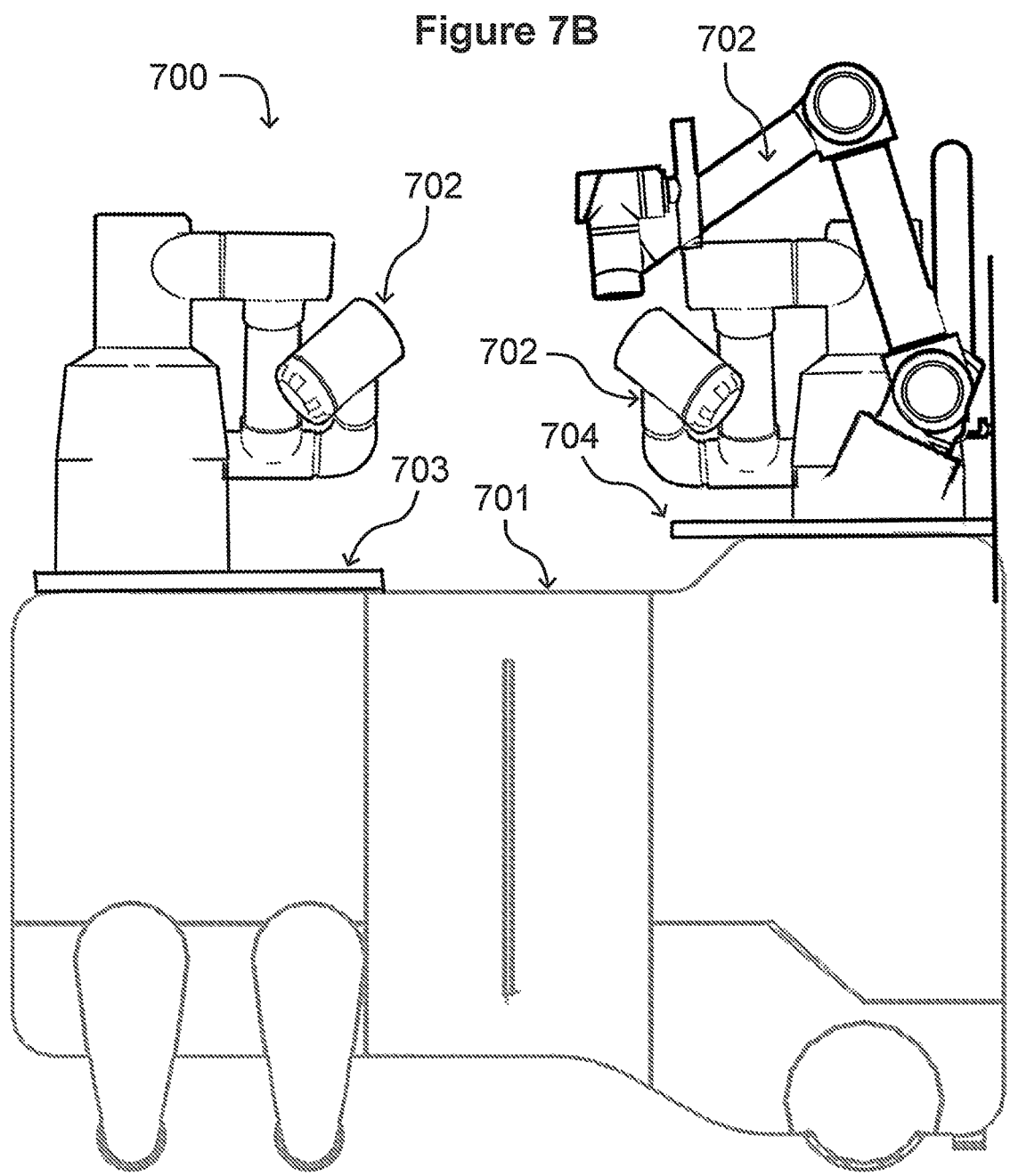

BILATERAL SURGICAL ROBOTIC SYSTEM

REFERENCE TO RELATED APPLICATIONS

This is a Continuation Application under 35 U.S.C. 111(a) of International Application PCT/162022/052297, filed Mar. 14, 2022, which claims the benefit of priority of U.S. Provisional Application 63/161,716, filed Mar. 16, 2021, and U.S. Provisional Application 63/253,533, filed Oct. 7, 2021.

FIELD OF THE INVENTION

The invention relates to a mobile bilateral surgical robotic system that may also include a robotically controlled and coordinated surgical navigation system. In particular, the invention relates to a low-profile mobile cart incorporating at least two robotic arms arranged on opposite sides of the surgical table where the mobile cart may be deployed under the surgical table. Multiple robotic elements, such as robotic arms, end effectors, cameras, imaging devices, tracking devices or other devices useful for robotic surgery can be included. Placement and movement of the robotic elements are controlled and coordinated by a single control unit, and wherein all of the robotic elements are based on a single rigid chassis and, thus, are robotically coordinated at a single origin point. Specifically, multiple robotic elements may be attached to, and controlled by, a single control unit and may be used in a coordinated fashion to deploy trackers, cameras and surgical instruments as part of a robotic surgery procedure. More particularly, in the context of robotic spinal surgery, multiple robotic elements may be attached to, and controlled by, a single control unit and may be used in a centrally coordinated fashion to deploy trackers, surgical instruments, hold one or more cameras, and carry out a surgical procedure, with the relative movements of each robotic element being coordinated by the central control unit. If desired, this single-chassis, multi-arm, robotically coordinated system may be augmented with robotic navigation technology.

BACKGROUND OF THE INVENTION

Robotic surgery is well known in the art, as is the application of robotic techniques to spinal surgery procedures such as pedicle screw placement. Many robotic surgery systems, such as the da Vinci robotic surgery system from Intuitive Surgical, are teleoperated. Multi-arm robotic surgical systems are available in the field, for example those provided by Cambridge Medical Robotics, but these known systems are often also teleoperated and are all comprised of single arms deployed separately with some level of coordination provided by a remotely-positioned control unit. Systems comprising multiple arms on multiple carts have significant drawbacks regarding integration into surgical workflow, along with an undesirably large footprint in the operating room. Also, in cases where these multi-arm systems do utilize a single cart, still the coordination between the arms is done by a physician who "closes the loop" with his eyes and hands while he sits in the control unit. Moreover, the control of teleoperated units by a remotely-positioned control unit does not provide the level of control required for a full range of surgical procedures, particularly in the case of spinal surgery. Accuracy will inevitably be inferior to a system where all robotic arms are fixed to, and coordinated by, a single chassis comprising a control unit.

Multi-arm robotic systems positioned under a surgical table have been disclosed, for example in US2018/0193101 to Hashimoto. However, such systems are not mobile and do not provide any disclosure of centralized control of robotic arm movement and navigation. Bed-mounted systems are also known, for example in US2010/0286712 to Won. However, such systems are, by definition, not mobile and also present significant obstacles to surgeon workflow and available space in the operating room. WO2020/079596 to Zehavi discloses another non-mobile robotic surgery system incorporating multiple arms for imaging and optional tool deployment. However, the robotic arms are floor mounted, large, would thus suffer from inferior accuracy and would be significantly disruptive of surgeon workflow and will bear high costs. None of these known systems provide a mobile solution with centralized control of robotic arm movement and navigation, and all deploy relatively large robotic arms that can suffer from lack of accuracy and low utilization and acceptance rate due to their size and the fact that they are not mobile.

Performance of a full range of spinal surgery procedures (beyond pedicle screw placement, which comprises a small fraction of most procedures), requires a bilateral system with highly accurate robotic arms and may also significantly benefit from robotically coordinated navigation. A typical procedure may require the placement of multiple passive or active markers on bone or on soft tissue, one or more robotically controlled and maneuvered cameras that can be placed at varying distances from the surgical field, and one or more end effectors deployed by robotic arms. Such a multi-arm/multi-camera system mounted on, and controlled by, one mobile cart, is not available in the current state of the art. There is a strong and long-felt need for such a system as it will enable the performance of a full range of spinal surgery procedures with robotically coordinated control and navigation at a level of accuracy not currently possible.

SUMMARY OF THE INVENTION

Provided herein is a bilateral robotic surgical system. The bilateral robotic surgical system comprises a mobile cart that is configured to be selectively placed under the surgical table, in particular under a spinal surgery table. The mobile cart incorporates at least 2 robotic arms, configured to be positioned on either side of the surgical table when in operation.

The mobile cart has a significantly lower profile than conventionally known systems wherein the robotic arms can be folded down from their deployment to the sides of the surgical table or, indeed, can be folded inside the cart itself. The low profile of the mobile cart and the ability to fold the arms inside the cart or to its side provides for the optional deployment of the mobile cart under the surgical table. This is a critical capability when it comes to sparing space in the operating room and to not having the system and its arms interfere with surgeon workflow.

The design of the mobile cart allows for relatively short, light robotic arms to be deployed on either side of the surgical table. This bilateral approach not only allows for the performance of a fuller range of robotic surgical procedures, and in particular spinal robotic surgical procedures, but it also enhances accuracy of the robotic arms. The relatively short, light robotic arms of the current inventive system are inherently more accurate than the larger arms of systems known in the art. In particular, systems that only have one tool-deploying robotic arm need to cover a much larger surgical field than the smaller arms of the present system, wherein each arm can carry a tool and cover a much smaller surgical field. Moreover, it is known in the art that a single robotic arm stretched to the farthest extent of its reach is less accurate in carrying out tasks than the same robotic arm used in a more folded deployment.

A key feature of the current inventive system is that the robotic arms originate from a common base. The common base also incorporates a central control unit. In this design, the movement of the robotic arms is centrally coordinated by the control unit of the common base. The benefit of the arms having a single point of origin is that the position and trajectory in space of all elements of the system, and their position and trajectory relative to each other, are known to the system. Therefore, the robotic system provided does not strictly speaking require navigation (as a localization method), although an optional choice to augment the system with navigation can be made.

In an alternative embodiment of the inventive system, the mobile cart may optionally comprise two constituent mobile units that may approach the surgical table from either side and may be joined together as they are deployed under the surgical table. In this embodiment, appropriate mechanical and electrical connections allow the two constituent mobile units to join together under the surgical table and form one mobile cart. Each constituent mobile unit houses one or more robotic arms that may be deployed from the side or top of the unit. Further in this embodiment, one of the constituent mobile units houses a central control unit that, once the mobile units are joined together, controls the deployment and movement of all of the robotic arms by way of the mechanical and electrical connections between the constituent mobile units. In this way, a single chassis mobile robotic surgical system is created from two constituent parts and is centrally controlled by a single control unit.

Also provided herein is a robotically controlled surgical navigation system to augment the bilateral robotic surgical system. Specifically provided herein is a robotically controlled surgical navigation system for robotic spinal surgery. The system is configured to perform all aspects of robotic spinal surgery procedures, beyond simple steps such as pedicle screw placement that are performed by currently known robotic systems.

In representative embodiments, the system comprises a central control unit housed by a surgical cart. At least two arms or other holders may be mounted to the cart. The at least two arms or holders are configured to hold cameras, end effectors or other instruments to be used in surgery, more particularly in spinal surgery. The at least two arms or holders may also be used to track passive or active markers in the surgical field, that are attached to soft or hard tissue, particularly preferentially to spinal bones, wherein the markers have usually been deployed by the physician or surgeon near the beginning of the surgical procedure. Active or passive markers may also optionally be attached to various relevant surfaces, such as the surgical table, surgical and assistive poles or stands and also the arms or holders themselves.

The inventive robotically coordinated surgical navigation system provides that the arms or other holders are centrally coordinated by the control unit housed in the surgical cart. Solely by way of example, this allows one arm or holder to be deploying a surgical instrument in relation to the bone marker while another arm or holder deploys a navigation/tracking camera at an appropriate distance and angulation, all of which allows for coordinated deployment of instruments and tracking of the markers. By way of further example, central control and coordination of multiple arms or holders by a control unit housed in a single cart allows for one or more cameras deployed at appropriate distances and angulations to be used for navigation during a surgical procedure in which one or more end effectors held by one or more robotic arms are caused to operate in the surgical field using guidance facilitated by the placement of multiple surgical instruments and devices in relation to passive or active markers.

One of the key features of various embodiments of the invention is that one or more navigation cameras can be mounted on one or more robotic arms, the movement of which are coordinated by the central control unit. Accordingly, the camera angulations are controlled and coordinated with the robotic system and the markers such that the markers can be visualized at an appropriate distance and angle. This approach prevents the disruption to surgeon workflow that would be created by bringing multiple robotic carts into the operating room. The approach also solves the problem commonly found in spinal surgery where cameras are kept at a larger distance from the surgical field (e.g., two or more meters), at which point larger markers must be used that obscure various aspects of the spine and/or surgical field. Larger markers may also move undesirably with respect to the bony anatomy as the anatomy shifts during surgery and the large markers deflect themselves and again, lose accuracy.

In robotically coordinated surgical navigation systems according to the present invention, multiple feedback loops are present. For example, in a first feedback loop, multiple robotic arms holding various instruments are deployed from the same cart as described above. These robotic arms are coordinated with each other and also with radiopaque markers (e.g. made of Tungsten material) on the anatomy by for example scanning the patient (x-ray, CT) while the radiopaque markers are attached to the bone and/or while at least one marker that is attached to at least one robotic arm is inside the scanned image.

Since the robotic arms are deployed on a single chassis with a single control unit, the movement of the robotic arms can be coordinated and the feedback loop between the arms is closed. More specifically, both robotic arms are able to be robotically accurate in relation to the bony anatomy by sharing the same common origin of axis and while using the robotic kinematics without the assistance of navigation as a localization method.

In a second exemplary feedback loop, all of a multiplicity of robotic arms that hold, for example, any desired mix of robotic navigation cameras, end effectors and surgical navigation markers or instruments, are disposed on a single chassis containing a single control unit that coordinates the movement of the robotic arms, thus closing this feedback loop.

In this regard, these robotically manipulated navigation cameras are not blindly seeking for the standard navigation markers but rather actively targeting the desired marker or location because the central controller knows where the target is from the image (e.g., CT) and the central controller coordinates the movement of the robotic navigation system to reach the target in an optimal distance and angulation.

In yet another example of a feedback loop, an active or passive marker may be placed on a robotic arm that is deployed on a single chassis along with other robotic arms that may hold robotic navigation cameras or end effectors. This third example of a feedback loop is closed because the single chassis has a control unit that coordinates the movement of the robotic arms and, for example, if the robotic navigation camera visualizes the marker on one or all of the robotic arms and the position of one or more of the robotic arms is changed accordingly, the feedback loop is closed.

All of these needs and elements benefit tremendously from the central coordination and control of the inventive single-cart, multi-arm, non-teleoperated robotic system.

BRIEF DESCRIPTION OF THE DRAWINGS

FIGS. 1*a-h* display various side and top views of a multi-arm, mobile surgical robotic system according to various embodiments of the present invention.

FIGS. 5*a-d* display various top and side views of surgical tool deployment of a multi-arm, mobile surgical robotic system according to various embodiments of the present invention.

FIG. 6 displays the deployment of a navigation modality of a multi-arm, mobile surgical robotic system according to various embodiments of the present invention.

FIGS. 7*a-b* displays side views of an alternate methodology of robotic arm deployment of a multi-arm, mobile surgical robotic system according to various embodiments of the present invention.

DETAILED DESCRIPTION OF THE INVENTION

Figure 1A:
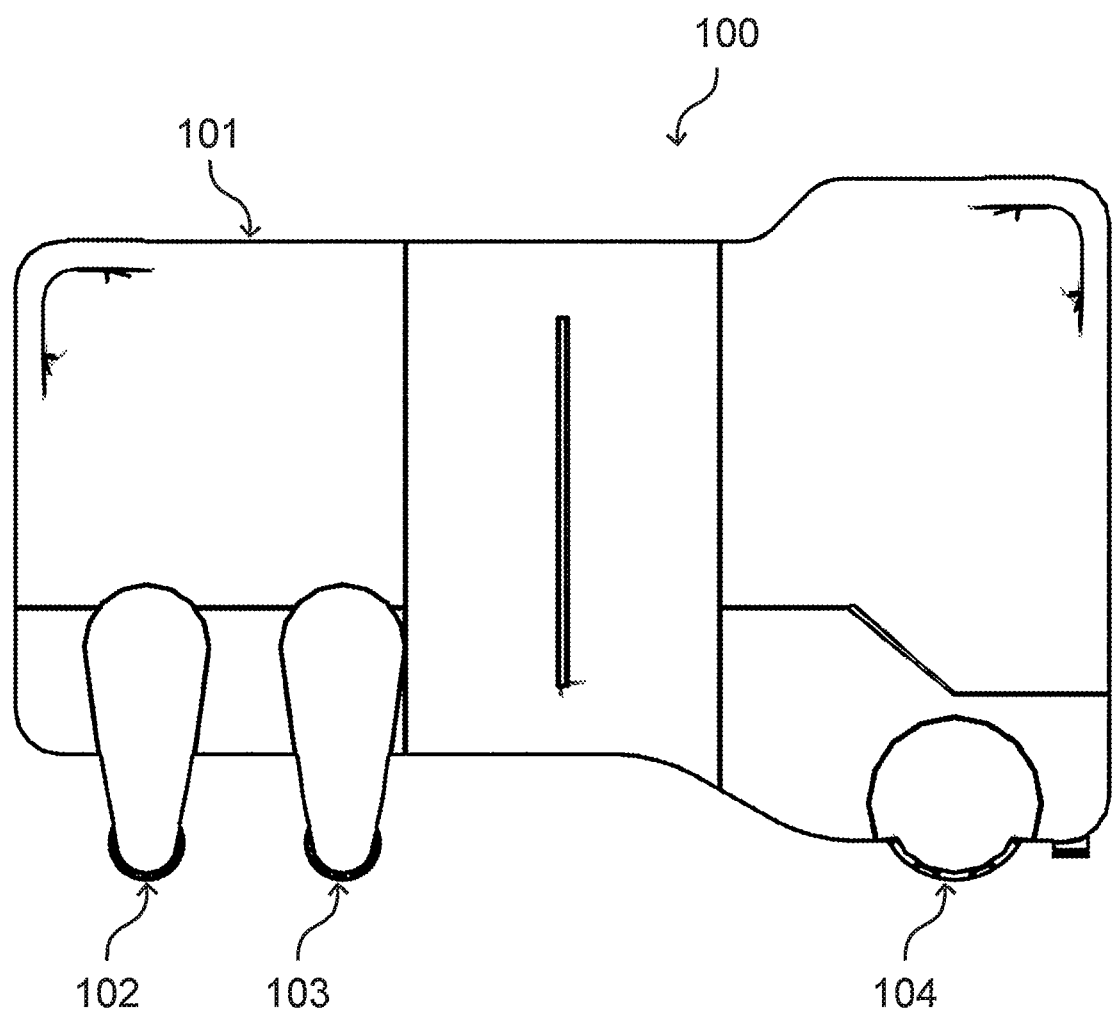
Figure 1C:
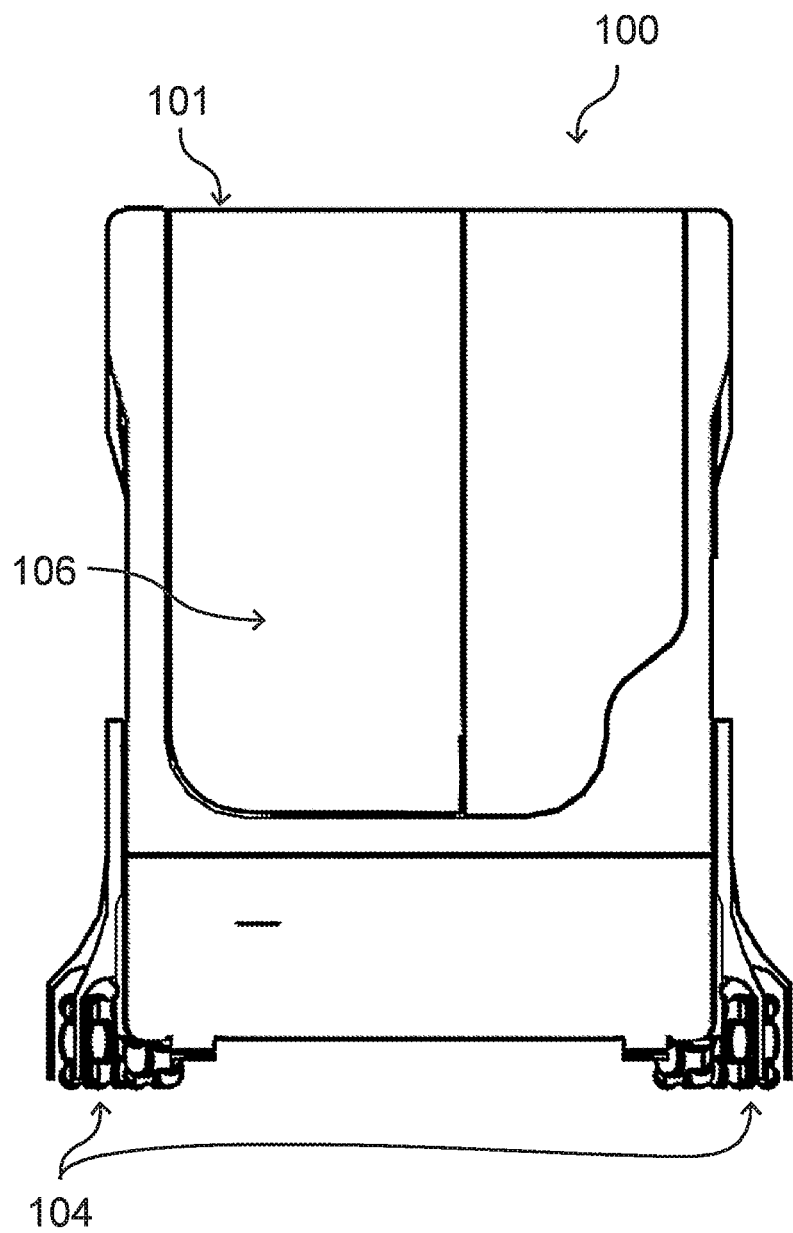
Figure 1H:
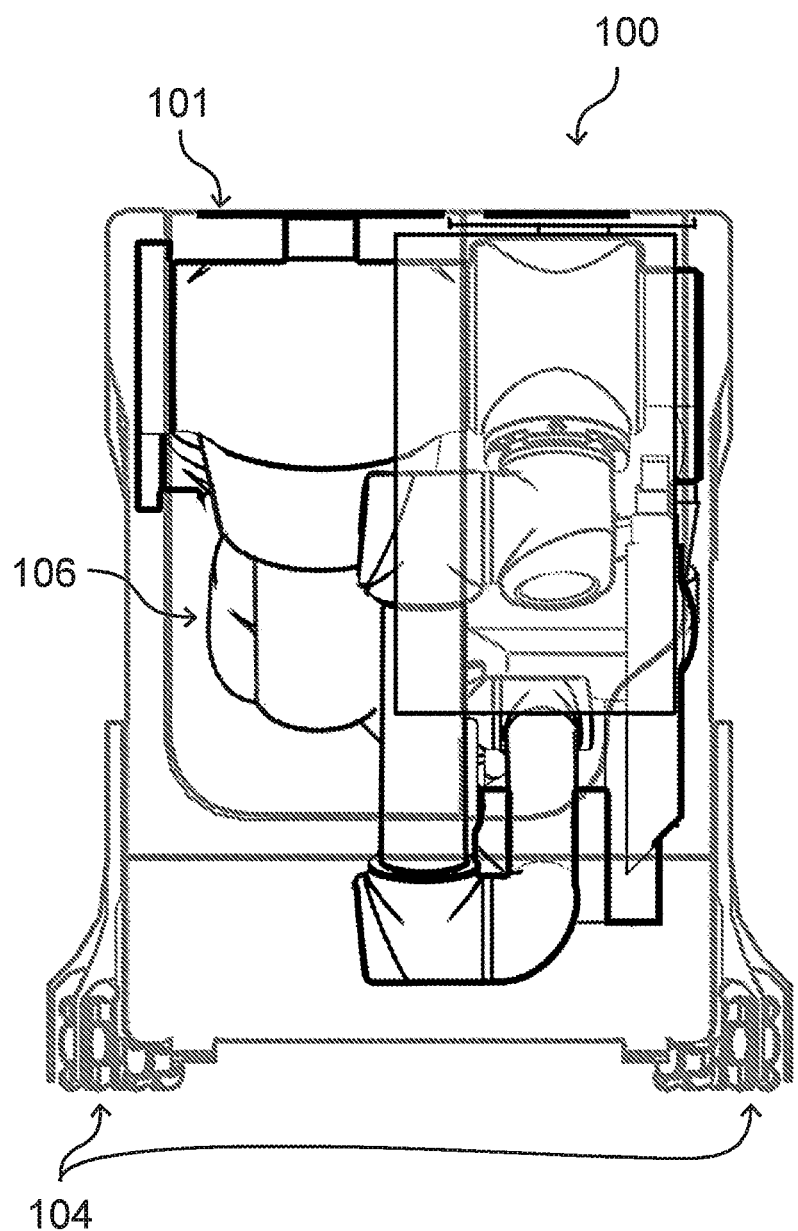

With reference now to the figures and several representative embodiments of the invention, the following detailed description is provided.

In one embodiment of the present invention, a mobile cart incorporating at least 2 robotic arms is provided, wherein at least one arm is positioned on each side of the surgical table. The mobile cart has a significantly lower profile than conventionally known systems so when the robotic arms are folded, the entire system can be deployed under any common surgical table (for example, approximately up to one meter high) in order to allow the robotic arms to be deployed on both sides of the surgical table and the patient lying on it. Placing the entire robotic system below the surgical table has significant value in sparing valuable operating room floor space and not interrupting the surgical team and their workflow.

In various embodiments, the robotic arms may be folded beside or inside the mobile cart in multiple ways. The arms may optionally be folded down beside the cart or may be folded into the cart, either into the sides of the cart or down into the top surface of the cart. Regardless of the folding modality, the desired end result is for the mobile cart with foldable arms to be easily deployable under the surgical table.

The cart is equipped with at least two pairs of wheels that facilitate the deployment and remove of the mobile cart under the surgical table. The pairs of wheels can be folded and/or retracted selectively to allow for obstacles, such as the longitudinal bar found under spinal surgery tables, to be navigated and crossed. In one embodiment, the cart is equipped with three pairs of wheels, two of the pairs being selectively retractable to allow for the cart to be deployed under a spinal surgery table.

In an alternative embodiment, the mobile cart may optionally comprise two constituent mobile units that may approach the surgical table from either side and may be joined together as they are deployed under the surgical table. This provides an alternate methodology for deployment under the surgical table that does not require pairs of wheels to be folded and/or retracted.

In this embodiment, appropriate mechanical and electrical connections allow the two constituent mobile units to join together under the surgical table and form one mobile cart with centralized control and communication capabilities. The connections between the two constituent units and the centralized control allow the robotic arms to be based on a single chassis and, thus, benefit from true centralized robotic control.

Each constituent mobile unit houses one or more robotic arms that may be deployed from the side or top of the unit. Further in this embodiment, one of the constituent mobile units houses a central control unit that, once the mobile units are joined together, controls the deployment and movement of all of the robotic arms by way of the mechanical and electrical connections between the constituent mobile units. In this way, a single chassis mobile robotic surgical system is created from two constituent parts and is centrally controlled by a single control unit. The robotic arms operate from a single origin with all of the accompanying benefits of a robotic system that "knows" where each of the arms are in three-dimensional space due to their common origin.

In various embodiments of the current inventive bilateral robotic surgical system, there is no requirement for the cart nor the robotic surgical arms to be affixed to the surgical table or to the floor. The wheels of the mobile cart can be locked to prevent movement. Also, optionally, an element of the cart can be deployed to press up against the bottom of the surgical table when the cart is deployed under the table, thus stabilizing the surgical table even when patient movement is taken into account and/or external forces are applied to the patient or table.

The cart serves as the common rigid base for the robotic arms and the precise location, trajectory and relation between the multiple robotic arms is known. Each robotic arm may have several degrees of freedom including height adjustment (Z axis) of its robotic base. Robot bases may also be equipped with rigid and accurate rails to provide two additional degrees of freedom (X-Y motion) in order to adjust the robot bases per specific case. This will allow the robot bases to be in the optimal position near the patient body (for example, approximately 10 cm from the patient's body).

One of the key novel elements of the following robotic system is that it can provide very large operating volume (trajectory coverage of up to 360 degrees around the designated organ), which is critical in some surgical areas like spine surgery, while using only two relatively small and short robotic arms (for example, up to one meter arm length). This is possible since it is required from each arm, on each table side, to cover by itself only part of the patient body—for example, the right side robotic arm is responsible for covering locations only on the right side/portion of the patient and the left side robotic arm is required to reach trajectories only in the left side/portion of the patient. Each robotic arm by itself is insufficient in covering the entire required surgical volume, but only both arms cooperating in conjunction with one another are sufficient to provide full surgical volume coverage. Moreover, even if for certain tasks one arm of one meter length can cover the required distance from one side of the table to the other side, than by stretching the arm to its full-length significant reduction in accuracy will occur. It is well known in the art that robotic arms are much more rigid and thus more accurate in their folded positions and less rigid and accurate at their extended/stretched positions. Other systems with single operating (non-navigation) robotic arms are required to deploy larger, heavier, less accurate robotic arms if significant surgical field coverage is desired.

The present robotic system can be incorporated with several localization techniques in order to provide the robotic controller the required coordinates for the robot's location in relation to the surgical target (e.g. the human spine), For example: Incorporating the suggested robotic system with a navigation system—either independently from the robotic system, as a $3^{rd}$ party system, or integrated within this system. Another option is performing x-ray scan or CT-scan while the robot holds a marker in the field of interest or a similar marker is fixed to the bony anatomy and by that acquiring the location of the robot end-effector in relation to the designated organ.

In a further embodiment, this bilateral robotic design is capable of solving several challenges which were not solved by other surgical systems thus far and specifically in spine surgery. First, the robotic arms are not attached to the table rail (as in some current systems known in the art) and by that they are not too close to the patient which can hurt the patient and/or limit the robotic motion by colliding with the patient body. On the other hand, they are also not too far from the patient like happens in other existing robotic systems in which the robotic arm is assembled on a cart which stands aside the table and by that requires the robot arm to be long, heavy and cumbersome in order to reach both sides of the patient from the same location (left and right portion of the body).

Also, since the system has at least one robotic arm deployed at each side of the table, each arm is required to perform tasks only on one side of the table, so this system can be equipped with relatively small/short and rigid robotic arms. This fact is critical from accuracy point of view and also these rigid arms will be able to perform additional tasks in spine surgery which require very high forces (e.g. vertebrae manipulation)—this topic will be further discussed in following sections.

In robotic surgery, in order to achieve and maintain high accuracy, it is critical to keep the distance between the robot base, the robot end effector and the operated organ, as small as possible. The following design enables exactly that not only in one side of the patient but in both sides simultaneously. Due to this design this critical bi-lateral "triangle of accuracy" is significantly smaller than all other available systems.

With the suggested design, short robotic arms positioned on a very low profile cart as described, are less likely to physically interrupt the surgical team and it will not block their view/sight. With this suggested design the robotic arms, even in their highest upwards working position, will almost never block the surgeon line of sight.

The novel bilateral robotic surgery system, due to its design, can also facilitate and enable the following robotic surgical activities, solely by way of example:

Performing bi-lateral and parallel surgical tasks simultaneously and/or sequentially on both sides of the patient (e.g., drilling a vertebra, inserting an implant etc.) This parallel work has additional critical importance from accuracy point of view. It is well known in spine surgery (for example) that due to the relative motion between one vertebra to the other it is difficult to maintain accuracy when working along the spine, from one vertebra to the next. One reason is that accuracy is diminished when moving further from the vertebra marked with the navigation marker (when using navigation system for robotic localization for example). Second reason is since when touching/drilling one vertebra it physically rotates and moves in relation to itself and it also moves in relation to the other vertebrae in the spine. The suggested system is capable of overcoming this challenge as described in the exemplary following sequence:

One robotic arm drills the first pedicle (first vertebra chosen for being the closest to the navigation system marker or the Imaging scan marker or any other localization method used in conjunction with this system) and places the pedicle screw with high accuracy. Leaving the robotic arm connected to the currently well anchored drill/implant and now this arm, while rigidly connected to the vertebra, is used as a stabilizer for the next vertebra/pedicle drilling-either in the same vertebra or the next vertebra (above or below). The system can then continue drilling and placing screws in "Zig-Zag" pattern—left and right/up and down while left drilling is stabilized by right grip and vise-versa.

Due to the fact that the robotic arms of the present system are short, strong and rigidly connected to the same rigid platform (the cart), these arms can hold the implants which are rigidly inserted to the pedicles of the vertebrae (for example) from both sides and manipulate the vertebrae in relation to each other. This technique can be used to manipulate 2 vertebrae (e.g. indirect decompression, compression, distraction etc.) or to several vertebrae together and even the entire spine. Having these arms located one in front of the other can enable them to distract two vertebrae by several millimeters and keep this distraction constant and safe while the surgeon is performing delicate surgical tasks between the vertebrae (e.g. disc removal, decompression etc.).

In alternative embodiments, it is possible to add to the system additional arms on each side, so while two opposite arms are occupied by retracting the two vertebrae, as described above, the third and forth arms are available to perform additional surgical tasks, either by human surgeon's guidance/control, or robotically controlled by software and algorithm guidance. Moreover, these anus, due to being short, strong and share the same rigid base, can optionally be attached to the metal rods (for example) which are part of the appliance and connecting the screws and perform manipulation on them by bending the rod and achieving the desired spine posture. This can not be achieved with any other surgical robotic system available. In this surgical approach, the fact that the robotic arms are deployed from both sides of the patient, are relatively low profile, are distant from each other but originate from a common base and are controlled by a central controller that knows the position of each arm, means that high force and high accuracy can be applied so as to safely bend the rod and manipulate the spine in vivo.

A similar technique of accurate and robust robotic boney manipulation is relevant to additional surgical areas like Hip/Knee replacement surgeries etc. the two strong arms which are robotically coordinated can hold and manipulate two pieces of bone (e.g., Femur, tibia etc.), while a third arm robotically synchronized with them, provides imaging, navigation etc. in order to augment the surgery and/or to assist the surgeon with multiple tasks while he is performing some surgical tasks in between. The third arm may also hold a surgical tool of some sort and these 3 or 4 surgical arms can automatically cooperate to perform robotically surgical tasks with or without human monitoring. The following is achieved mainly due to the fact that all these arms are robotically coordinated using a single rigid chassis and still being easy to handle under normal economical and Human-machine-interface (HMI) considerations.

Anatomy target(s) and markers can then be acquired by intra-operative imaging (e.g., intraoperative CT). In this example, a robotic navigation camera is used that is mounted on a robotic arm that is, in turn, affixed to a single chassis with a control unit. The single chassis may have one or more robotic arms mounted to it that are used for surgical tasks. The control unit coordinates the movement of the multiple robotic arms and, thus, the navigation camera toward the anatomy target, creating a closed feedback loop. The use of a navigation camera provides both redundancy and diversity of information about the anatomical targets of interest, which is crucial for accuracy and overall adequacy of information. The camera may employ different technologies, for example infra-red and optical (RGB) modalities. The use of different modalities also provides diversity of information, thus increasing overall accuracy and quality of the provided information.

In the same working example, a further robotic navigation camera may be mounted on a further robotic arm mounted to the same single chassis, wherein the further camera is positioned at a conventional distance from the surgical field (e.g., 1-2 meters), so that the whole surgical field may be imaged. Additional robotic arms may be disposed on the single chassis and may hold markers or end effectors. Due to the fact that all of the robotic arms are disposed on the same chassis and that their movement is coordinated by the control unit contained in the chassis, one of skill in the art will realize that the movement of each of the various arms is related to the movement of the other robotic arms in a closed feedback loop. For example, if one of the robotic arms is holding a navigation camera close to its anatomical region of interest (e.g., a particular vertebra) based on the position of a marker, then the navigation camera held at a conventional distance can visualize the entire surgical field and assist in the placement of the other close-in navigation cameras adjacent to their anatomical regions of interest (e.g., adjacent vertebrae with markers already placed on them). This closed feedback loop can then be used to guide the deployment of a surgical tool that may be robotically brought to the surgical field as an end effector on a robotic arm mounted to the single chassis or may be manually brought to the surgical field by a surgeon. In either the robotic or non-robotic scenario, the robotic navigation camera held at a conventional distance from the surgical field may assist in deployment of the surgical tool by virtue of its view of the entire surgical field in the optimal distance and angulation for each and every specific scenario and its inherent ability to robotically maneuver itself to overcome obstacles and interferences that obscure its path.

One of skill in the art will understand that the optical navigation modality specifically disclosed herein is but one possibility for augmentation of navigation capabilities to the current inventive system. The skilled artisan will be aware of other navigation modalities, such as, solely by way of example, EM navigation and ultrasound navigation, each of which could be incorporated into the current inventive system in a similar manner according to techniques known in the art.

While the present applicants have disclosed embodiments of the inventive system with two surgical arms (i.e., robotic arms deploying surgical tools) and one navigation arm (i.e., a robotic arm holding a navigation camera), it is also possible to have an embodiment of the present inventive system with one surgical arm and one navigation arm. Such two-arm embodiments could dispose the navigation arm and the surgical arm on opposite ends of the cart to provide a bilateral system, but the navigation arm and the surgical arm could also be disposed on the same end of the cart. In either scenario of arm placement in this two-arm system, the mobile cart of the current inventive system would still deploy under the surgical table as described, thus providing the disclosed advantages of mobility and lack of interference with surgeon workflow.

We now make specific reference to the attached drawings. One of skill in the art will easily understand that the attached drawings are merely representative of embodiments of the present invention. The skilled artisan will understand that variations to the described embodiments could easily be made without departing from their spirit or intent and such variations would still fall within the scope of the current disclosure. Solely by way of example, many of the attached drawings show a mobile robotic system with three robotic arms, but one of skill in the art will understand that more or less robotic arms could be deployed. By way of further example, many of the attached drawings show a mobile robotic system with three sets of retractable wheels that facilitate deployment of the mobile robotic cart under a surgical table. However, one of skill in the art will realize that any combination of wheels or similar mechanisms that allow the mobile cart to deploy under a surgical table and, in particular, a spinal surgical table, will fall within the scope of the current invention.

One of skill in the art will also realize that any known and available surgical robotic arms could be deployed on a mobile robotic system according to the current invention. The present inventors are not claiming proprietary rights over particular robotic arms, but rather have invented a mobile surgical robotic system where multiple robotic arms arc deployed and controlled from a common base, thus providing the significant advantages over the current state of the art as explained herein. The skilled artisan would appreciate and be able to choose the type of robotic arms that could be used in conjunction with the present invention.

One of skill in the art will also understand and be able to choose the type and scale of materials required to assemble the current inventive system once they have reviewed the current disclosure. The skilled artisan will know the type of materials that are commercially acceptable in surgical robotic systems and will be aware of the control systems and associated software that would be required to assemble and operate the currently disclosed inventive system.

FIGS. 1*a-h* display various side and top views of a multi-arm, mobile surgical robotic system 100 according to various embodiments of the present invention. A mobile surgical robotic system 100 is shown embodied in a mobile cart 101. The cart 101 has 3 sets of wheels 102, 103, 104 that are selectively retractable to facilitate movement of the cart 101 around, for example, an operating room. The retractable nature of the wheels 102, 103, 104 allows the cart 101 to navigate over obstacles, for example the longitudinal bar found under a spinal surgical table.

The cart 101 of FIGS. 1*a-h* has a set of doors 105 at one end and a set of doors 106 at the other end for enclosure and deployment of one or more robotic arms 107, 108, 109. As shown, the cart 101 encloses three robotic arms 107, 108, 109 that may be optionally folded into the cart 101 or deployed from the ends of the cart 101 when the doors are opened. As already discussed herein, the cart 101 forms a common base for the robotic arms 107, 108, 109. The robotic arms 107, 108, 109 originate from the common base and their selective deployment is managed by a central control unit that is also situated in the cart 101.

Figure 2A:
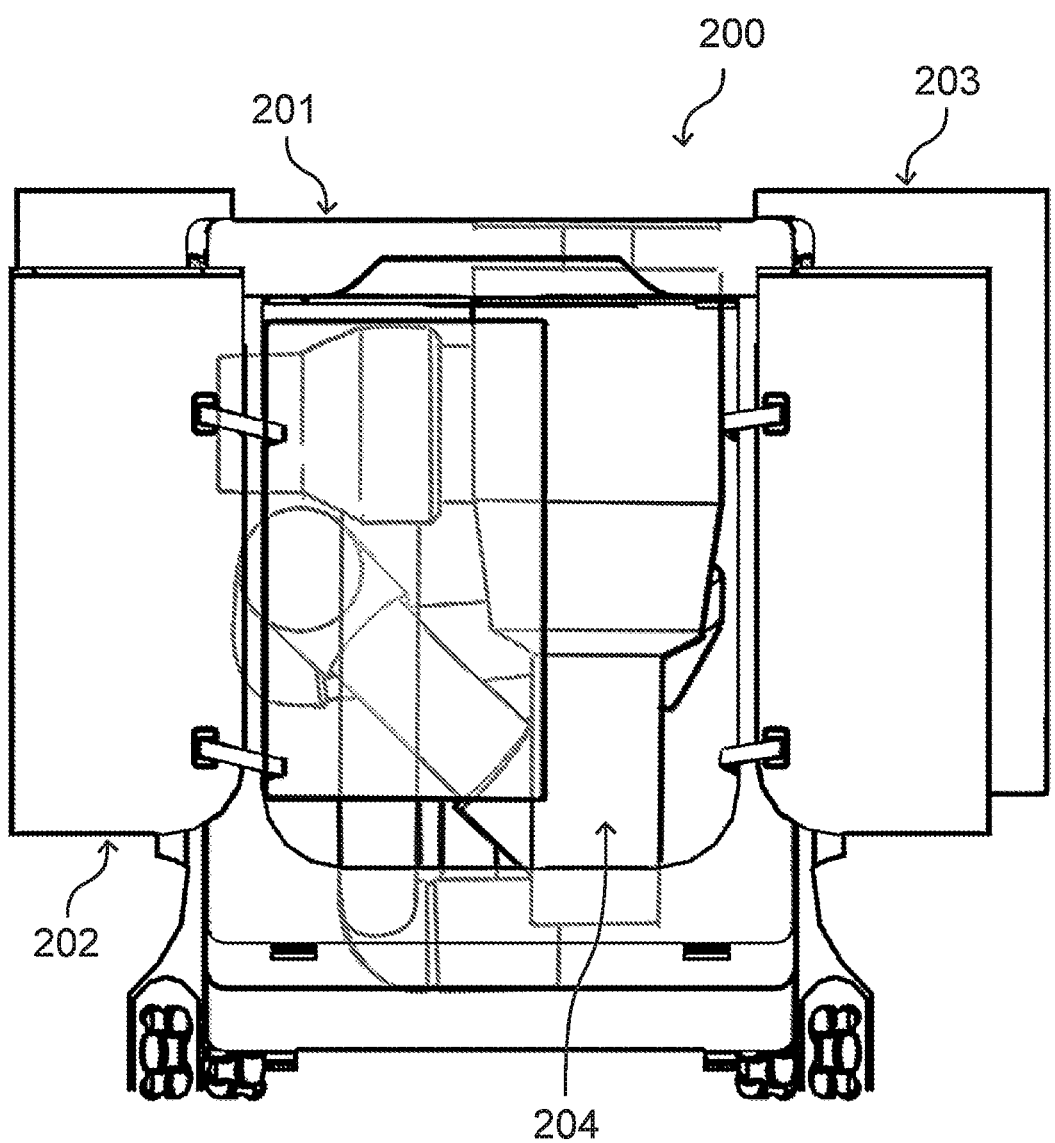
FIGS. 2 *a-b* display two side views of side door operation of a multi-arm, mobile surgical robotic system according to various embodiments of the present invention.
Figure 2B:
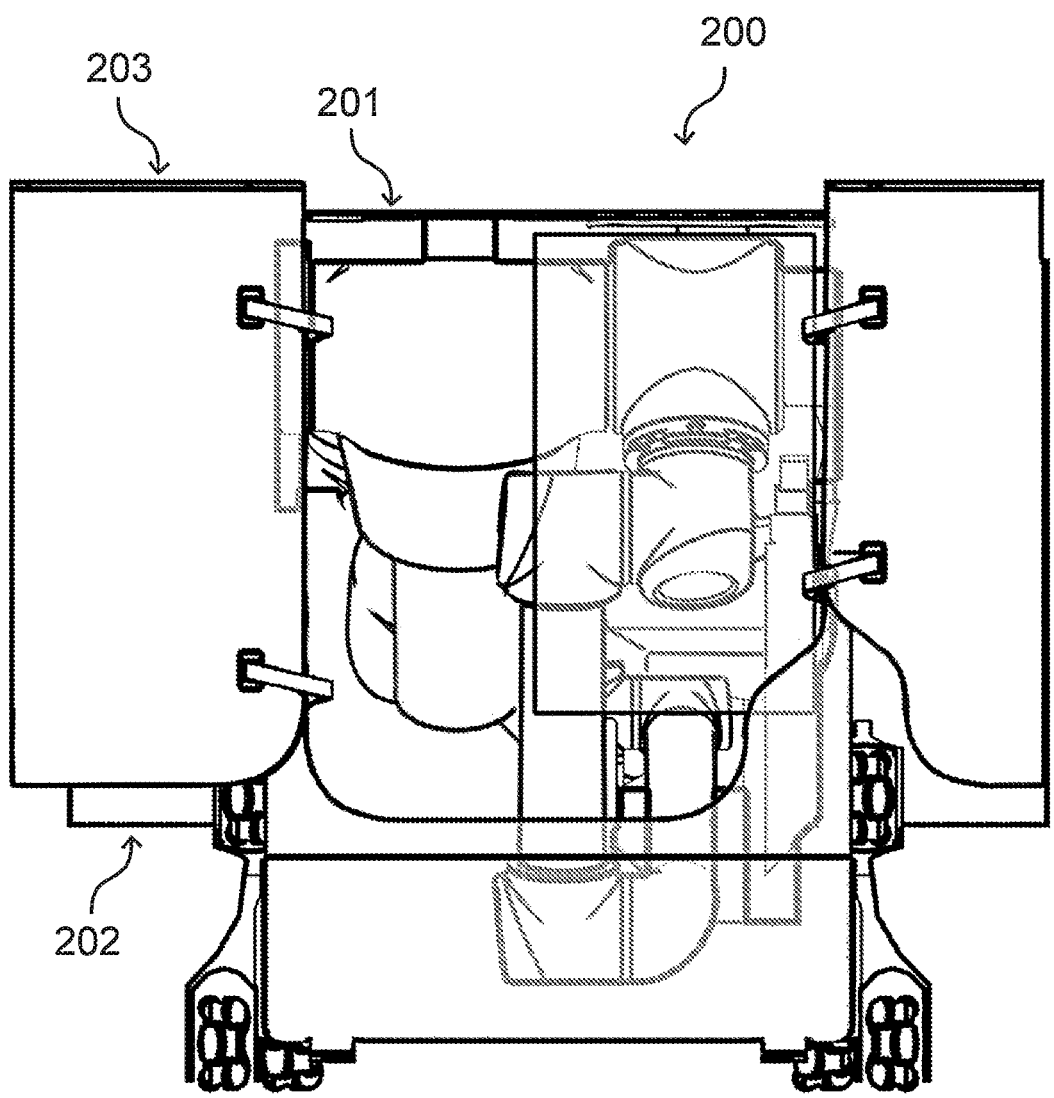

FIGS. 2a-b display two side views of side door operation of a multi-arm, mobile surgical robotic system 200 according to various embodiments of the present invention. As shown in FIGS. 2a and b, the cart 201 of the mobile surgical robotic system 200 has a set of doors 202, 203 positioned at each end of the cart 201 in the views provided here, one or more robotic arms 204 are folded into each end of the cart 201 and the doors 202, 203 can be selectively opened to allow for deployment of the robotic arms 204.

Figure 3A:
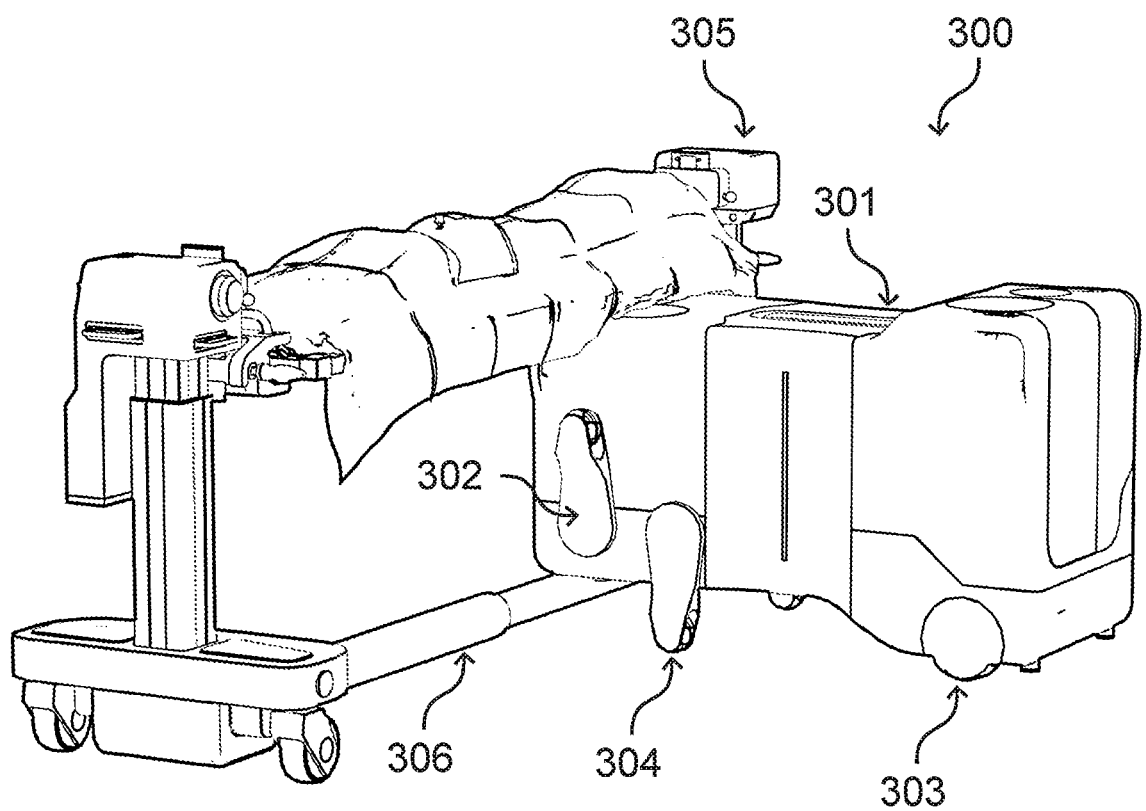
FIGS. 3 *a-c* display alternate side views of wheel deployment of a multi-arm, mobile surgical robotic system according to various embodiments of the present invention.
Figure 3B:
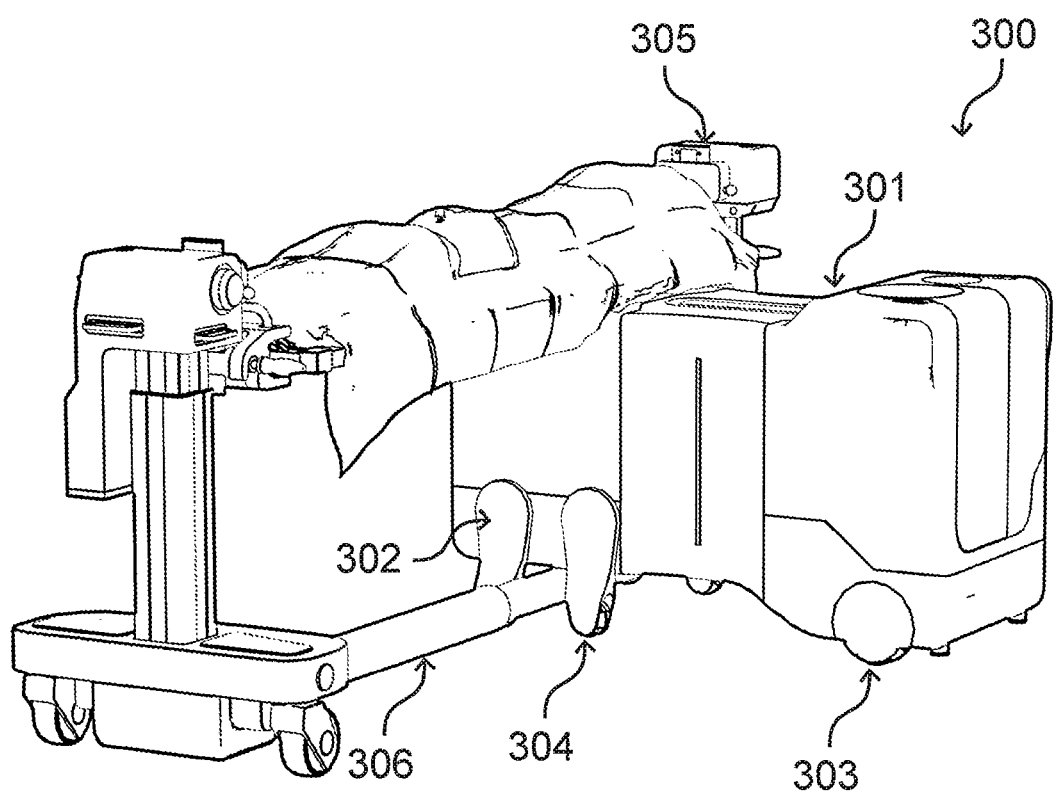
Figure 3C:
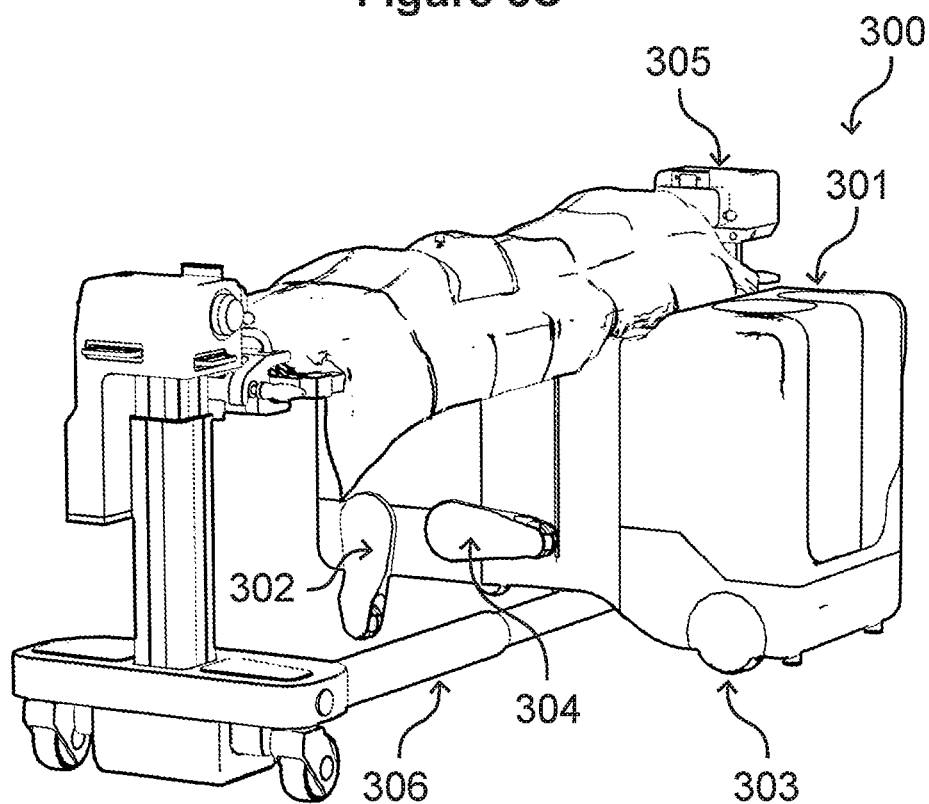

FIGS. 3a-c display alternate side views of wheel deployment of a multi-arm, mobile surgical robotic system 300 according to various embodiments of the present invention. In FIGS. 3a-c, the cart 301 of the mobile surgical robotic system 300 has a first set of wheels 302 near one end of the cart 301, a second set of wheels 303 near the other end of the cart 301 and a third set of wheels 304 on the same side of a midline as the first set of wheels 302. With this design setup, the mobile cart 301 of the current invention is able to deploy under a surgical table 305 that may have obstacles in the way, such as the longitudinal bar 306 found on almost all conventional spinal surgical tables. As shown in FIG. 3a, as the cart 301 approaches the longitudinal bar 306 under the spinal surgical table, the first set of wheels 302 can be retracted, while the other two sets of wheels 303, 304 stay in contact with the floor. As then shown in FIG. 3b, once the vertical plane of the first set of wheels 302 has cleared the bar 306, the first set of wheels 302 can be returned to contact with the floor. Finally, as shown in FIG. 3c, the third set of wheels 304 can then be retracted to allow for advancement and centering of the mobile cart 301 under the surgical table 305. Since two sets of wheels are always in contact with the floor, the cart 301 remains mobile and stable.

Figure 4A:
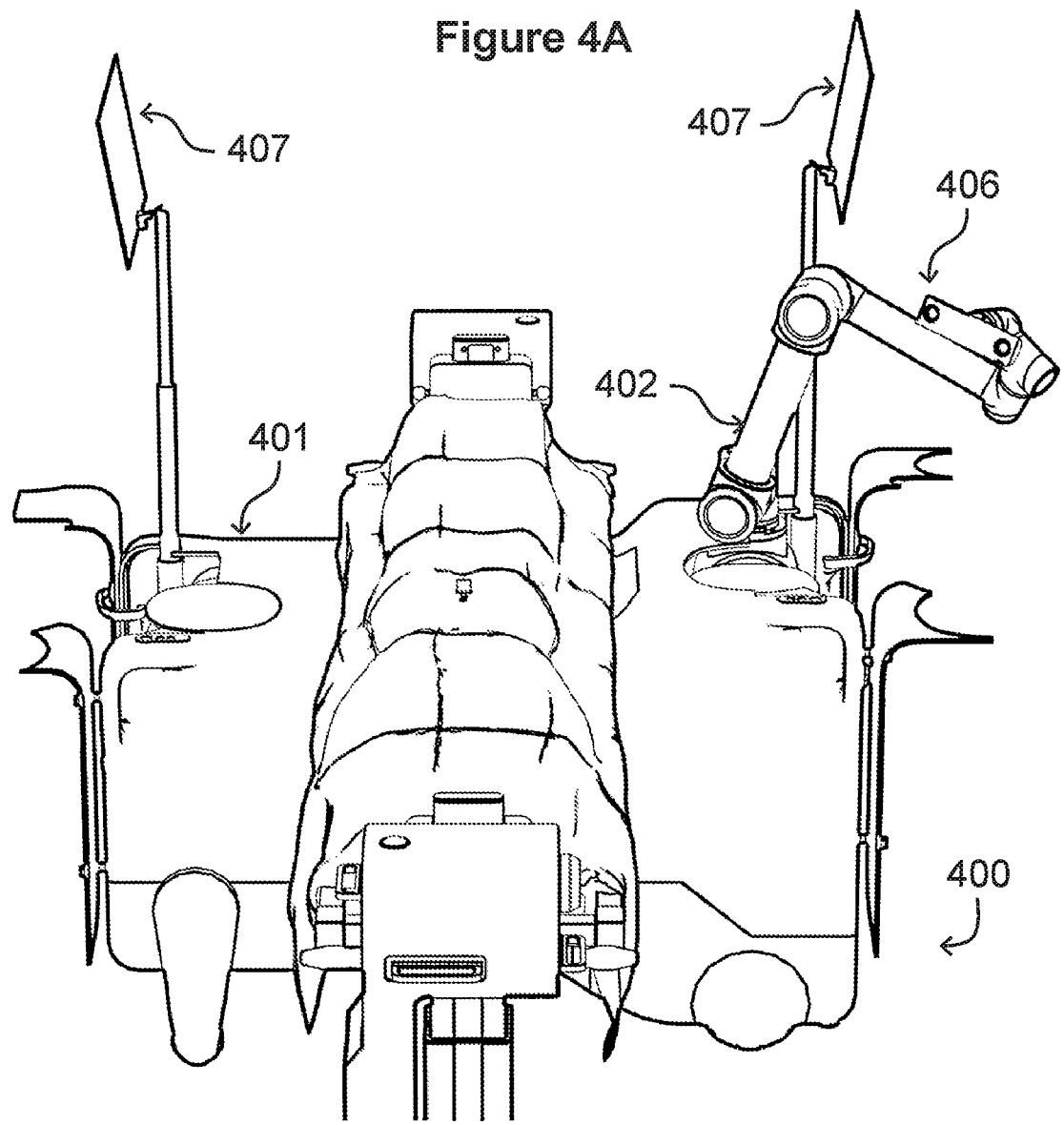
FIGS. 4 *a-g* display various top, side and end views of robotic arm deployment of a multi-arm, mobile surgical robotic system according to various embodiments of the present invention.
Figure 4B:
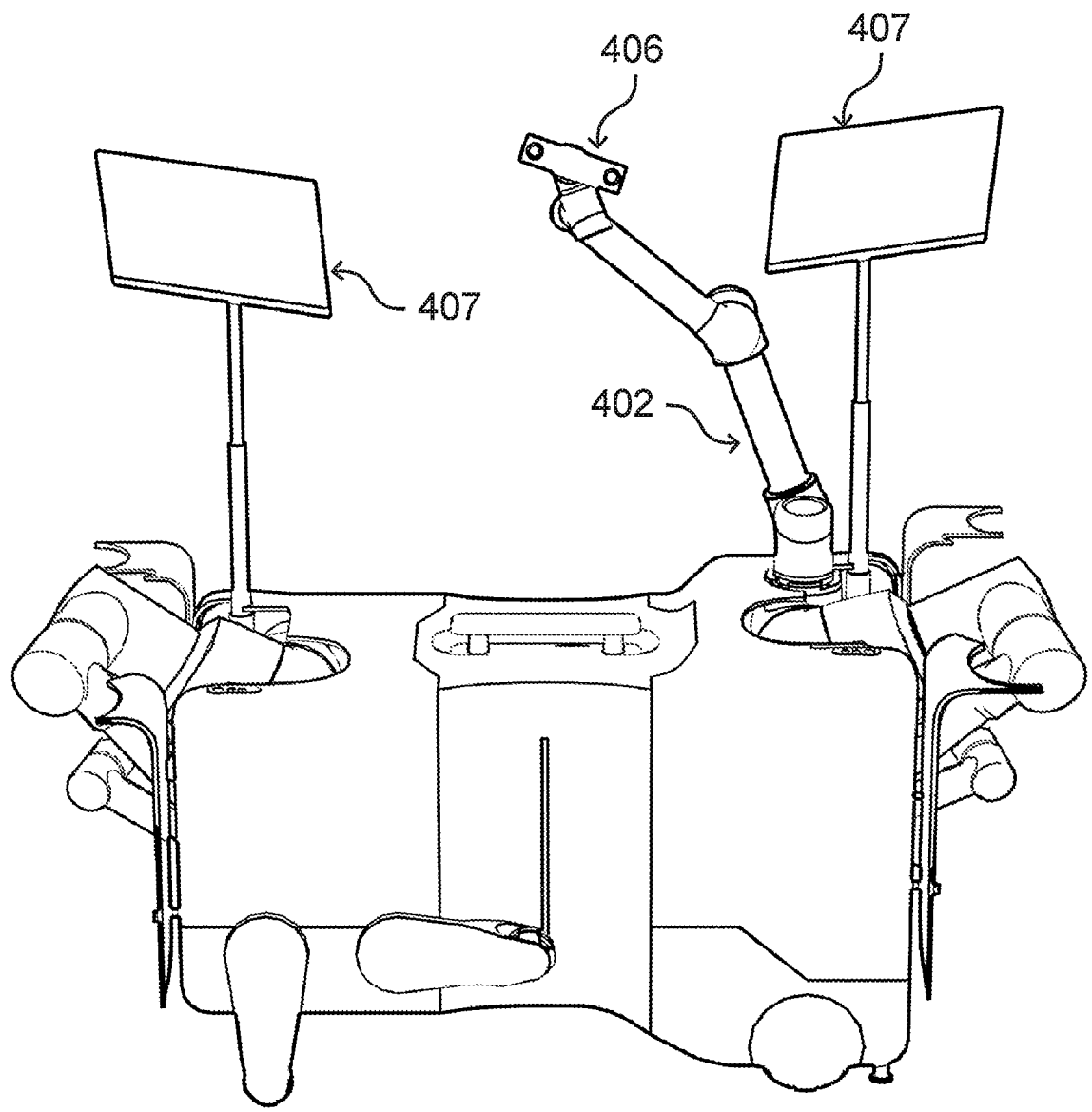
Figure 4C:
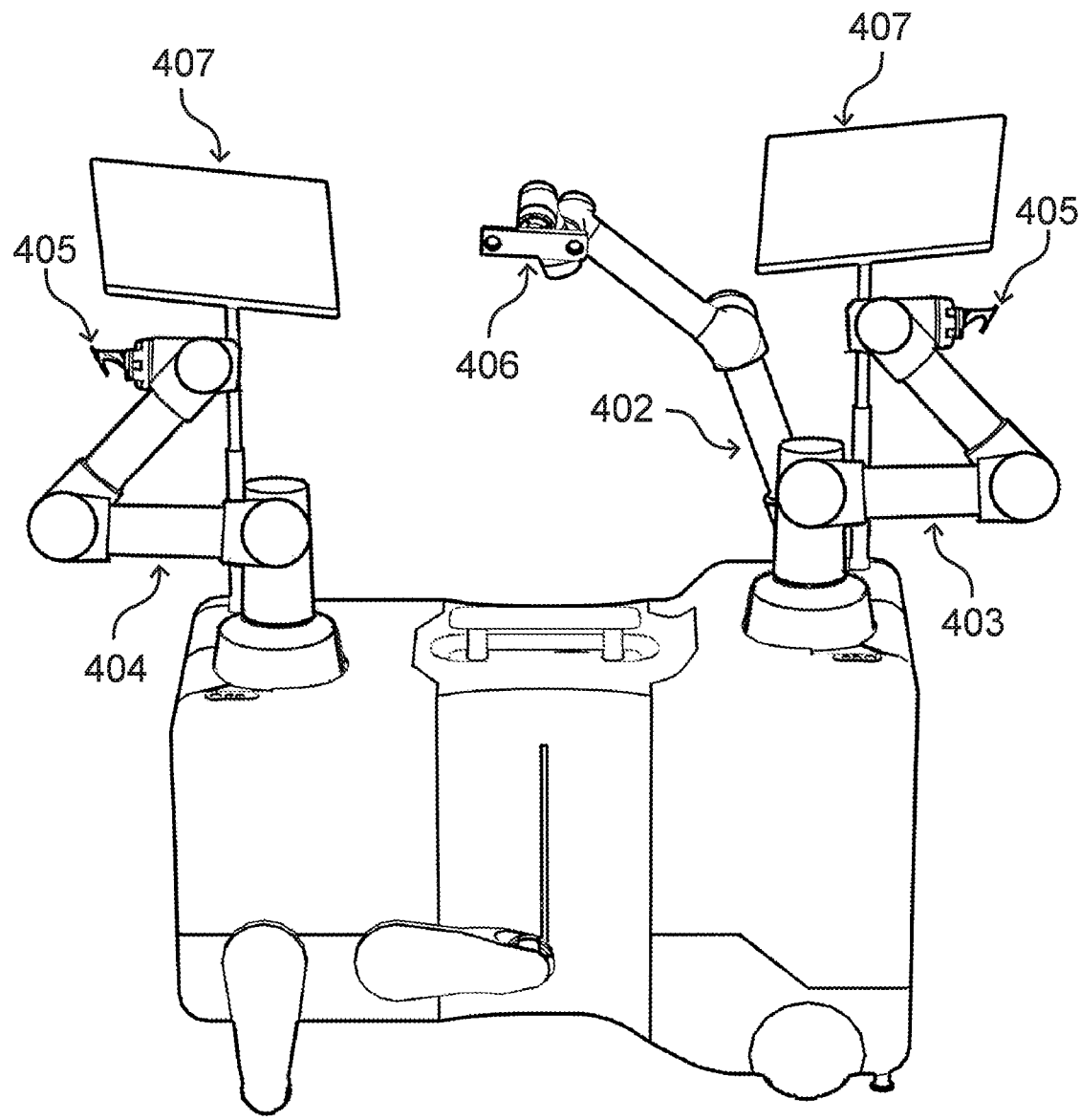
Figure 4D:
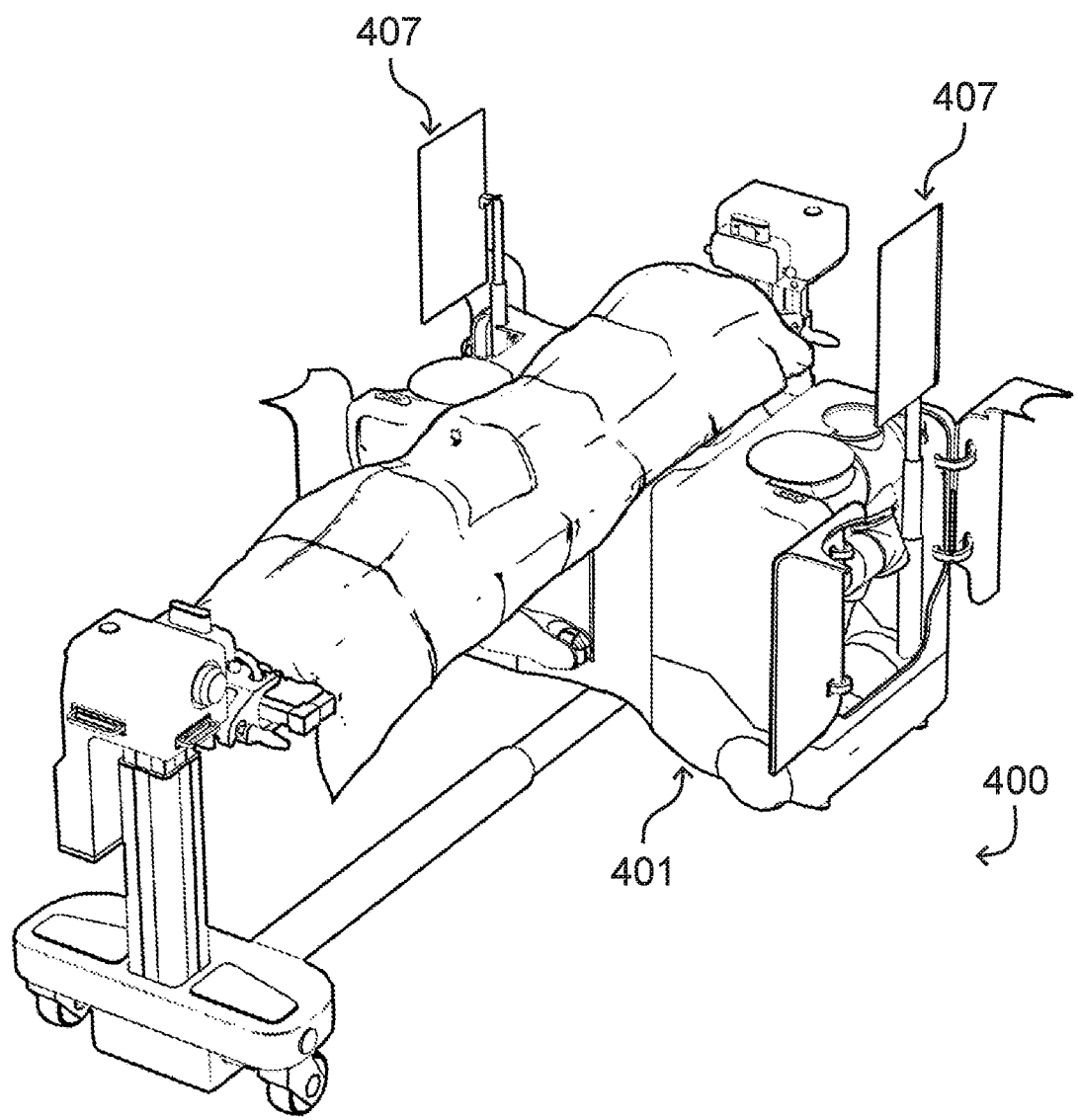
Figure 4E:
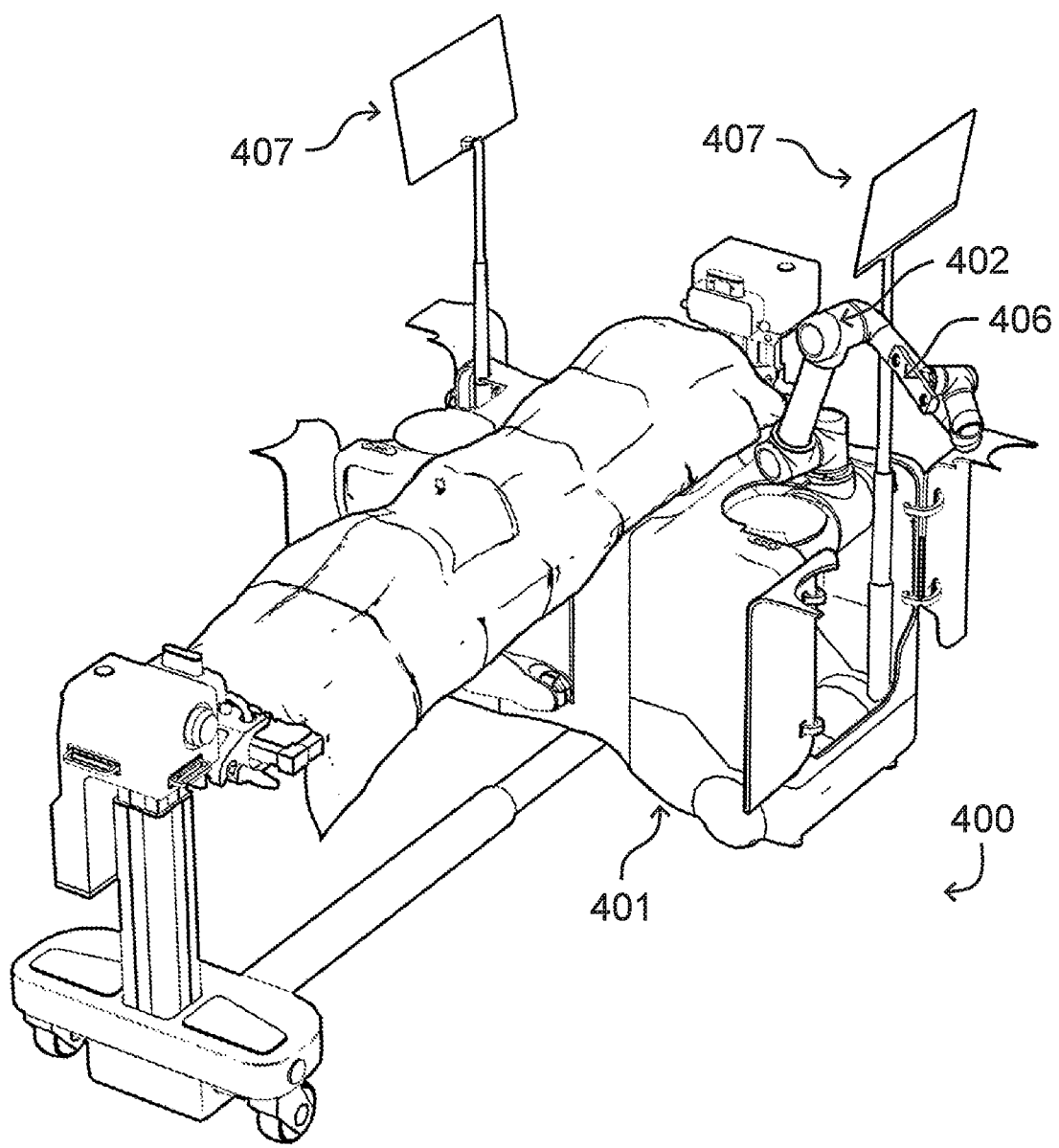
Figure 4F:
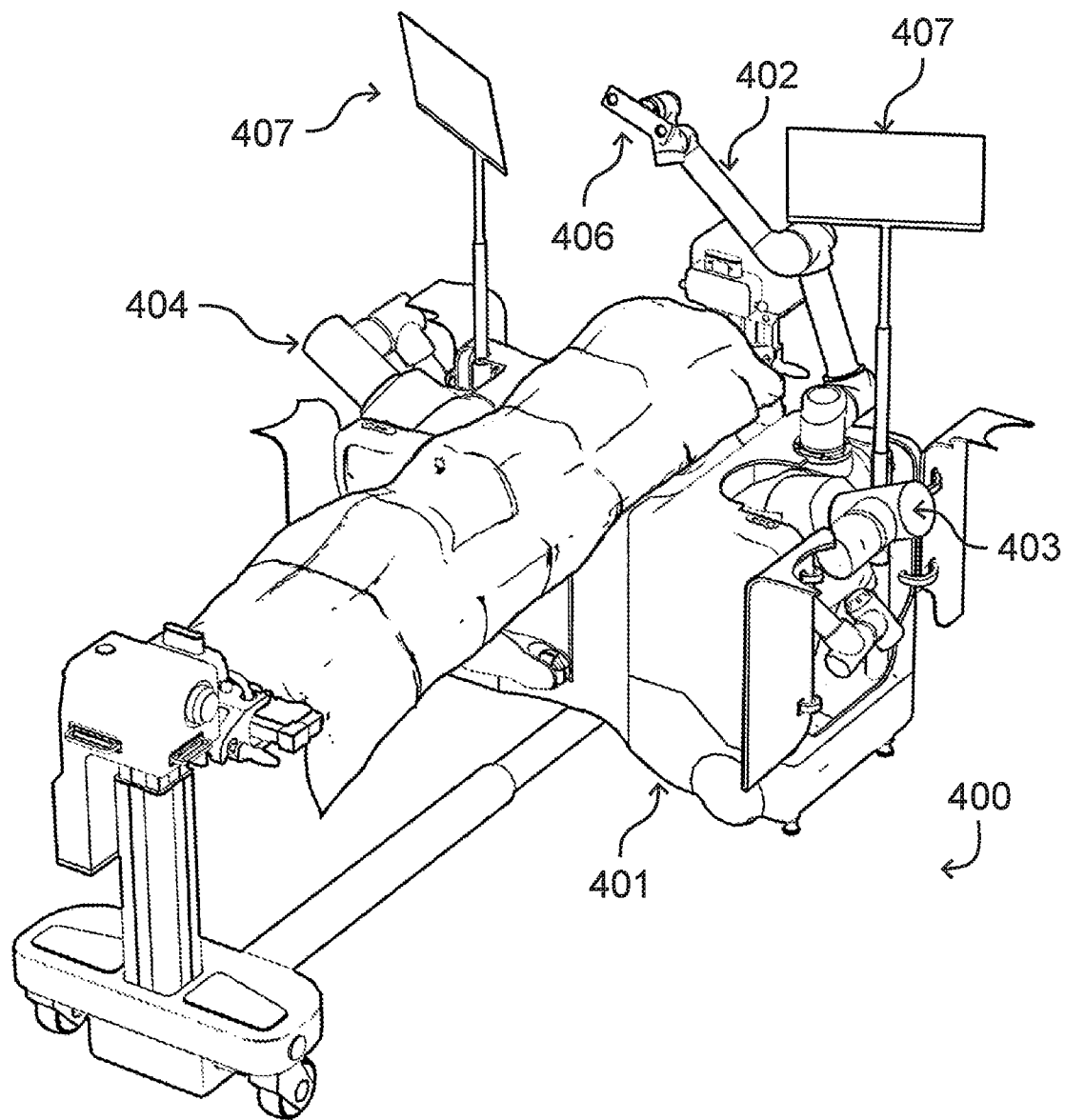
Figure 4G:
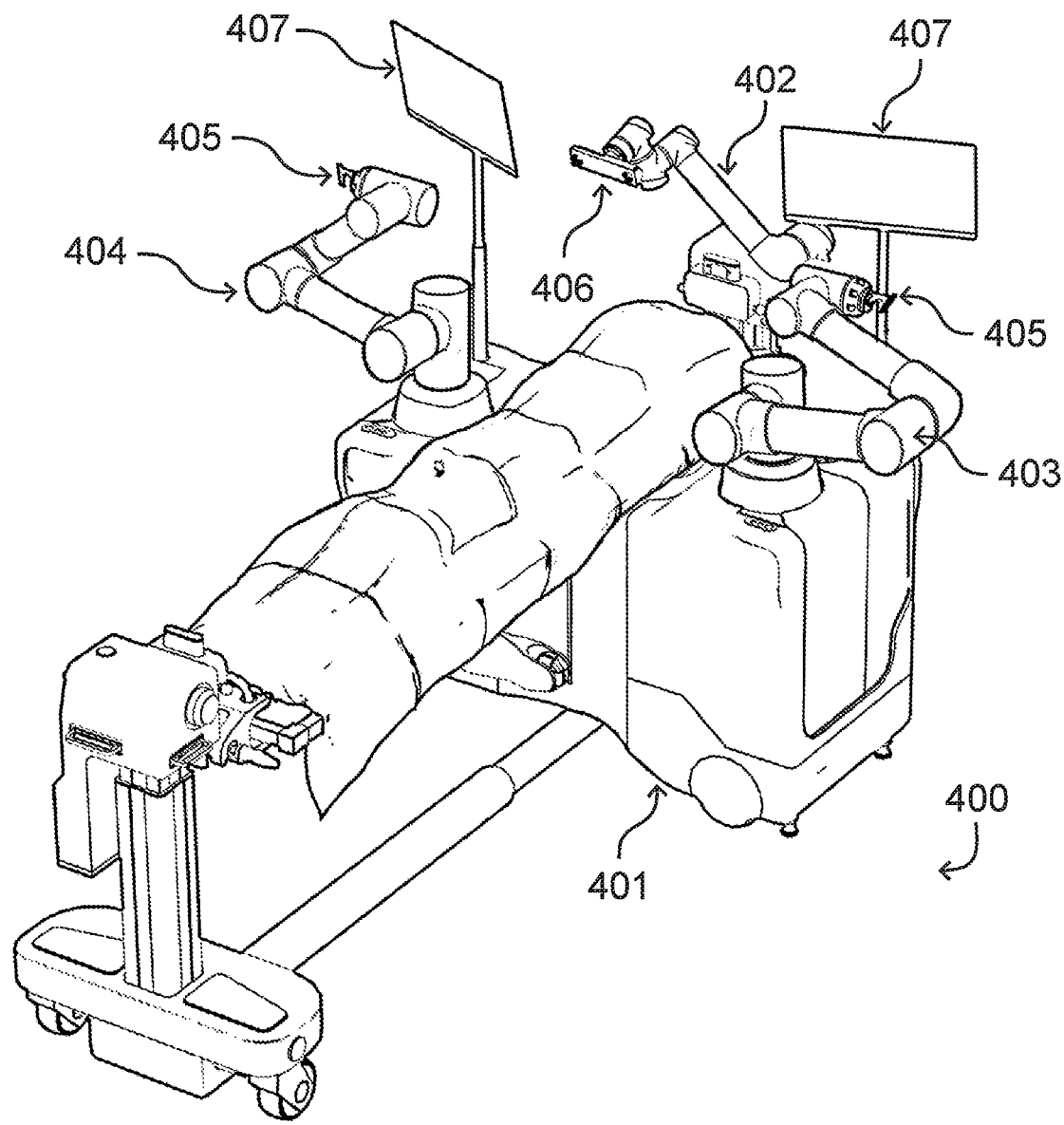
Figure 5A:
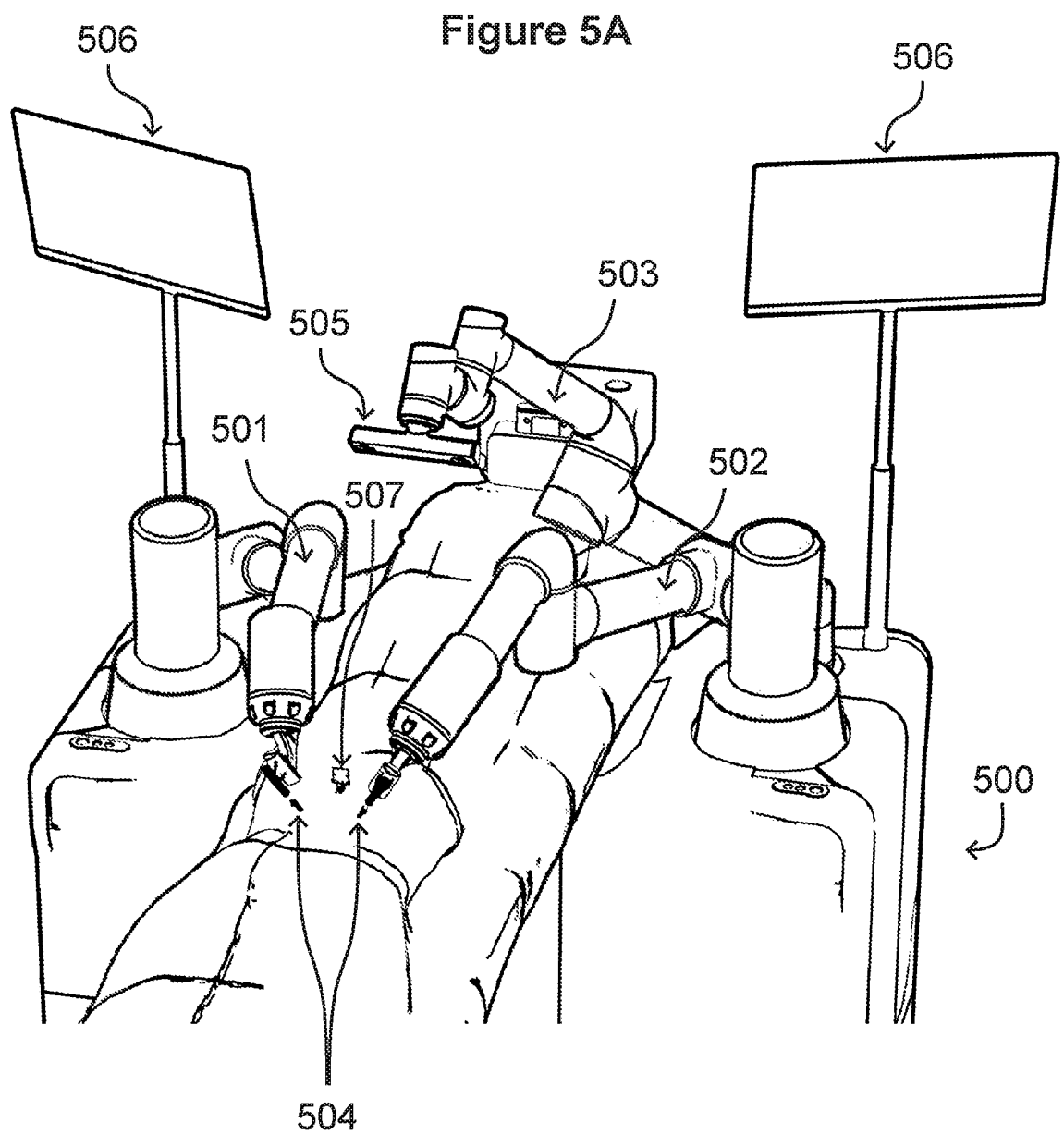
Figure 5C:
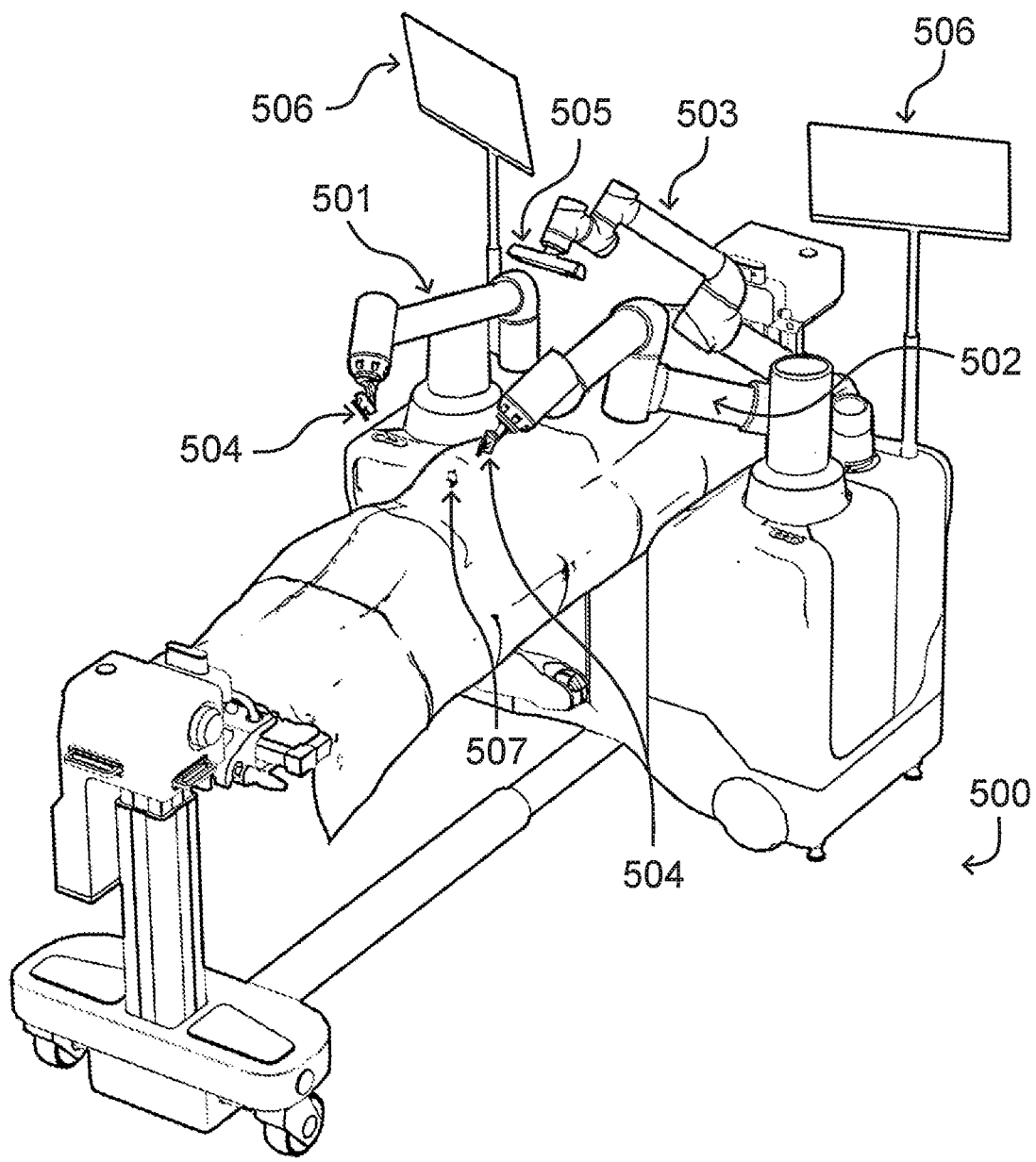
Figure 5D:
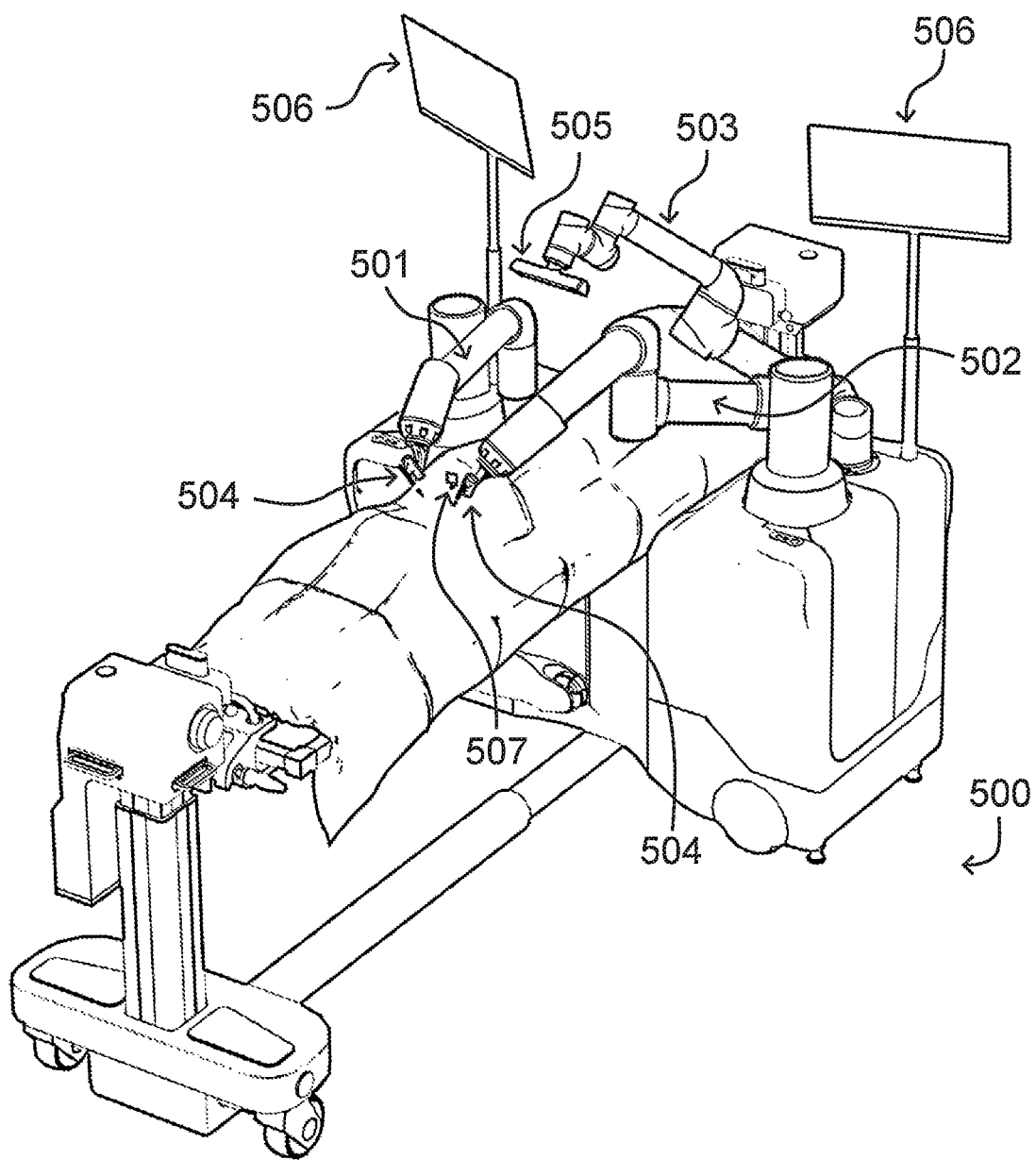

FIGS. 4a-g display various top, side and end views of robotic arm deployment of a multi-arm, mobile surgical robotic system 400 according to various embodiments of the present invention. The various views found in this series of figures show partial and full deployment of multiple robotic arms as they are deployed through the open doors of the cart 401. For example, FIG. 4c shows an embodiment of the mobile surgical robotic system 400 of the current invention with three robotic arms 402, 403, 404 deployed. Two of the robotic arms 403, 404 are holding surgical tools 405 while a third robotic arm 402 is holding a navigation camera 406. In addition, two screens 407 are shown in FIG. 4c that provide various options for the user to interface with the inventive system 400.

FIGS. 4d-g show more pull-away top views of the deployment of robotic arms from the mobile cart of the mobile surgical robotic system 400 of the present invention. These figures provide a more holistic view of the various stages of arm and screen deployment when using the inventive system. FIGS. 4d-g show three robotic arms 402, 403, 404 being deployed, two 403, 404 holding surgical tools 405 and one 402 holding a navigation camera 406, along with two screens 407 for the user to interact with the system. One of skill in the art will of course understand that variations in the number of robotic arms and screens will be possible without departing from the spirit and substance of the current disclosure.

FIGS. 5a-d display various top and side views of surgical tool deployment of a multi-arm, mobile surgical robotic system 500 according to various embodiments of the present invention. In FIGS. 5a-d, two robotic arms 501, 502 are shown holding surgical tools 504 and one robotic arm 503 is shown holding a navigation camera 505. Two screens 506 for interacting with the system 500 are also shown. These figures show that relatively short and robust robotic arms can be deployed, one from each side of the patient, with each robotic arm being able to independently advance a surgical tool toward target anatomy of a patient. As discussed herein, this provides significant advantages in terms of reach, stability and accuracy of the robotic arms and allows for a much wider range of surgical procedures to be performed. The robotic arms all originate from the same origin on the cart, thus allowing the inventive mobile surgical robotic system to know the location of the robotic arms in space and with respect to each other at all times. Additional navigation capabilities are thus not strictly required.

FIGS. 5a-d also show a single surgical marker 507 that is attached to the anatomy of the patient. The navigation camera 505 that is mounted on one of the robotic arms 503 can visualize the marker 507. Since the navigation camera 505 is mounted to a robotic arm 503 that originates from the same common point (the cart) as the other robotic arms 501, 502, the inventive mobile surgical robotic system 500 is able to incorporate information from the navigation camera 505 in its guidance of the surgical robotic arms 501, 502 holding the surgical tools 504. As discussed herein, the coordination of all three robotic arms by the central control unit of the inventive system provides for centralized robotic coordination that, in turn, provides for increased accuracy and usability.

FIG. 6 displays the deployment of a navigation modality of a multi-arm, mobile surgical robotic system 600 according to various embodiments of the present invention. In FIG. 6, a radiopaque surgical maker 601 is attached to the bony anatomy of a patient. One of the robotic arms 602 of the current mobile surgical robotic system 600 holds an additional marker 603 above the target bony anatomy of the patient and an intraoperative CT system 604 is deployed to obtain an image of the surgical field that includes the aforementioned markers 601, 603. In this regard, the location in space of the bony anatomy of the patient is obtained, along with the position of the end effector of the robotic arm 602 holding the marker 603. As described herein, because all of the robotic arms of the current system originate from the same common origin on the cart of the system, the inventive mobile surgical robotic system is now registered to the target anatomy of the patient and the central control unit can guide movement of the robotic arms (along with attached tools and end effectors) to the target anatomy during performance of the surgical procedure, additionally using information taken from the navigation camera (that is also co-registered since it is mounted on a robotic arm originating from the same common base on the cart. The registration step can be repeated as desired during a surgical procedure when, for example, the target anatomy shifts or the surgeon wishes to operate on a different region of anatomy.

FIGS. 7a-b displays side views of an alternate methodology of robotic arm deployment of a multi-arm, mobile surgical robotic system 700 according to various embodiments of the present invention. FIG. 7a shows the robotic arms 702 folded into the mobile cart 701 of the inventive mobile surgical robotic system. The robotic arms 702 on each side of the cart 701 are deployed on platforms 703, 704 that are selectively movable in the vertical plane to optionally be deployed inside or to the upper exterior of the cart 701. FIG. 7b shows the platforms 703, 704 raised out of the cart 701 and the robotic arms 702 thus deployed to the exterior of the cart 701. One of skill in the art will realize that this deployment strategy may provide advantages in some use cases. Deployment of the robotic arms 702 in this manner may be simpler from a mechanical perspective since multiple side doors are not required. Also, deployment of the arms 702 in this manner may also allow for top doors to be more easily closed after the robotic arms are deployed to protect the interior of the cart from fluids and debris that may be present during a surgical procedure.

One of skill in the art will realize that several variations on the disclosed embodiments are possible while staying within the bounds of the current invention. Solely by way of example, different variations in the number of navigation cameras, robotic arms, markers and end effectors can be used without departing from the invention. As another example, markers of varying sizes can be used. The embodiments provided are representative in nature.

What is claimed is:

1. A mobile surgical robotic system for use with a surgical table having a head, a foot, and opposed lateral sides and being positioned on a supporting structure in an operating room with a floor, said mobile surgical robotic system comprising:
    a single chassis having opposite ends and configured to be removably positioned under the surgical table, wherein said opposite ends are configured to extend beyond the opposed lateral sides of the surgical table when said single chassis is positioned under the surgical table at a location between the head and foot of the surgical table;
    at least two robotic arms disposed on the single chassis with at least one robotic arm disposed on each of the opposite ends of the single chassis; and
    a central control unit disposed on the single chassis for robotically coordinating movement of the at least two robotic arms;
    wherein the single chassis is configured to be moved independently of the surgical table and to be manually positioned over the floor between a location remote from the surgical table and a location under and across a width of the surgical table to locate at least one robotic arm on each side of the surgical table.

2. The mobile surgical robotic system of claim 1, wherein the at least two robotic arms are configured to be contained within the single chassis for storage and during positioning under the surgical table and wherein the at least two robotic arms are configured to be deployed from the single chassis after it is positioned under the surgical table for use during the surgical procedure.

3. The mobile surgical robotic system of claim 2, wherein the two robotic arms are configured to be folded into their respective opposite ends of the single chassis during storage and positioning of the mobile surgical robotic system under the surgical table.

4. The mobile surgical robotic system of claim 2, wherein the at least two robotic arms are disposed on platforms within the single chassis and wherein said platforms are configured to be raised or lowered to selectively deploy the robotic arms from their respective sides of the single chassis.

5. The mobile surgical robotic system of claim 1, further comprising a monitor screen configured to allow a user to interface with the central controller of the mobile surgical robotic system.

6. The mobile surgical robotic system of claim 5, wherein the central controller of the mobile surgical robotic system is configured to perform bilateral spinal surgical procedures without assistance of navigation cameras or other imaging equipment.

7. The mobile surgical robotic system of claim 5, comprising at least three robotic arms and wherein at least one of the at least three robotic arms is mounted with a robotic navigation cameras.

8. The mobile surgical robotic system of claim 7, further comprising a radiopaque marker configured to be placed on an anatomy of a patient.

9. The mobile surgical robotic system of claim 8, wherein one of the at least three robotic arms is configured to position a marker between the radiopaque marker and the robotic navigation camera to allow the central controller to register the mobile surgical robotic system with the anatomy of the patient.

10. The mobile surgical robotic system of claim 9, wherein the central control unit is configured to robotically coordinate movement of the at least two robotic arms holding surgical tools and the at least one arm mounted with a robotic navigation camera procedure after the mobile surgical robotic system has been registered with the anatomy of the patient.

11. The mobile surgical robotic system of claim 1, further comprising at least three sets of wheels for moving the mobile surgical robotic system wherein one or more of the at least three sets of wheels is selectively retractable.

12. The mobile surgical robotic system of claim 11, wherein the mobile surgical robotic system is configured such that the one or more retractable sets of wheels are retracted and re-deployed during positioning of the system under the surgical table.

13. The mobile surgical robotic system of claim 12, wherein the single chassis is configured to apply pressure to an underside of the surgical table for fixing the position of the mobile surgical robotic system relative to the surgical table.

14. The mobile surgical robotic system of claim 1, wherein the central controller of the mobile surgical robotic system is configured to be operated by a user located at the surgical table.

15. A mobile surgical robotic system for use with a surgical table having a head, a foot, and opposed lateral sides and being positioned on a supporting structure, comprising:
    a single chassis having opposite ends and configured to be removably positioned under the surgical table, wherein said opposite ends are configured to extend beyond the opposed lateral sides of the surgical table when said single chassis is positioned under the surgical table at a location between the head and foot of the surgical table;
    two robotic arms disposed on the single chassis with one of the two robotic arms disposed on each of the opposite ends of the single chassis, wherein a first of the two robotic arms is configured to hold a surgical tool and a second of the two robotic arms is configured to hold a navigation modality; and
    a central control unit disposed on the single chassis for robotically coordinating the movement of the two robotic arms;
    wherein the single chassis is configured to be moved independently of the surgical table and to be manually positioned over the floor between a location remote from the surgical table and a location under and across a width of the surgical table to locate at least one robotic arm on each side of the surgical table.

16. The mobile surgical robotic system of claim 15, wherein the two robotic arms are configured to be contained within the single chassis for storage and during positioning under the surgical table and wherein the two robotic arms are configured to be deployed from the single chassis after said chassis is positioned under the surgical table for use during the surgical procedure.

* * * * *